United States Patent [19]

Labrie

[11] Patent Number: 5,550,107
[45] Date of Patent: Aug. 27, 1996

[54] COMBINATION THERAPY FOR THE TREATMENT OF ESTROGEN-SENSITIVE DISEASE

[75] Inventor: Fernand Labrie, Quebec, Canada

[73] Assignee: Endorecherche Inc., Quebec, Canada

[21] Appl. No.: 785,890

[22] Filed: Nov. 4, 1991

Related U.S. Application Data

[63] Continuation of Ser. No. 321,926, Mar. 10, 1989, abandoned.

[51] Int. Cl.⁶ .................. A61K 38/00; A61K 31/56; A61K 31/495; A61K 31/50; A61K 31/445; A61K 31/165; A61K 31/135

[52] U.S. Cl. ................. 514/11; 514/15; 514/169; 514/170; 514/161; 514/255; 514/328; 514/649; 514/617

[58] Field of Search .................. 514/11, 15, 169, 514/170, 171, 255, 328, 617, 649

[56] References Cited

U.S. PATENT DOCUMENTS

| | | | |
|---|---|---|---|
| 3,061,616 | 10/1962 | Camero et al. | 260/397.4 |
| 3,127,427 | 3/1964 | Boller et al. | 260/397.4 |
| 3,752,814 | 8/1973 | Fluckiger et al. | 544/346 |
| 4,024,248 | 5/1977 | Konig et al. | 424/177 |
| 4,071,622 | 1/1978 | Johnson et al. | 424/177 |
| 4,094,994 | 6/1978 | Schonenberger et al. | 424/341 |
| 4,100,274 | 7/1979 | Dutta et al. | 424/177 |
| 4,118,483 | 10/1979 | Konig et al. | 424/177 |
| 4,472,382 | 9/1984 | Labrie et al. | 424/177 |
| 4,481,190 | 11/1984 | Nestor et al. | 424/177 |
| 4,650,787 | 3/1987 | Schally et al. | 514/11 |
| 4,732,912 | 3/1988 | Pilgrim et al. | 514/510 |
| 4,751,240 | 6/1988 | Bowler et al. | 514/510 |
| 4,760,053 | 7/1988 | Labrie | 514/15 |
| 4,760,061 | 7/1988 | Edwards et al. | 514/211 |
| 4,775,660 | 10/1988 | Labrie et al. | 514/15 |
| 4,775,661 | 10/1988 | Labrie | 514/15 |

FOREIGN PATENT DOCUMENTS

| | | | |
|---|---|---|---|
| 58481 | 8/1982 | European Pat. Off. | |
| 78158 | 5/1983 | European Pat. Off. | |
| 0138504 | 4/1985 | European Pat. Off. | 514/169 |
| 0151326 | 8/1985 | European Pat. Off. | |
| 209066 | 1/1988 | New Zealand | |
| 222761 | 10/1989 | New Zealand | |
| 223088 | 1/1991 | New Zealand | |
| 8601105 | 2/1986 | WIPO | 514/171 |

OTHER PUBLICATIONS

Adair, *Surg. Gynecol. Obstet.* 84:719–722 (1947).
Adair, et al., *JAMA* 140:1193–2000 (1949).
Adair, et al., *Ann. Surg.* 123:1023–1035 (1946).
Beardwell et al., *Cancer Chemo. Pharmacol.* 10(3):158–160 (1983).
Brodie, et al., *Steroids* 38:693–702 (1981).
Bryan et al., *Cancer* 54:2436–2440 (1984).
Bucourt, et al., *J. Biol. Chem.* 253:8221–8228 (1978).
Centola, *Cancer Res.* 45:6264–6267 (1985).
Chan, et al., (1987) *Biochem. Biophys. Res. Comm.* 144(1):166–171.
Cooperative Breast Cancer Group, *JAMA* 188:1069–1072 (1964).
Corbin, et al., (1984) *J. Steroid Biochem.*, 20(6B):1369, No. A9.
Covey, et al., *Cancer Res.* 42:3327s–3333s (1982).
Coy, et al., *J. Med. Chem.* 19(3):423–425 (1976).
Dutta, et al., *J. Med. Chem.* 21(10):1018–1024 (1978).
Engelsman, et al., *Brit. J. Cancer* 30:177 (1975).
Erchegyi, et al., *Biochem. Biophys. Res. Comm.* 100(3):915–920 (1981).
Ernshaw, et al., *Clin. Endo.* 21:13–21 (1984).
Giudici, et al., *J. Steroid Biochem.* 30:391–394 (1988).
Goldenberg, et al., *JAMA* 223:1267–1268 (1973).
Henderson, et al., *J. Steroid Biochem.* 24:303–306 (1986).
Hilf, *Handbook of Experimental Pharmacology* 43:191–210 (1976).
Kennedy, et al., *Geriatrics* 25:106–112 (1970).
Kennedy, et al., *Cancer* 21:197–201 (1967).
Klijn, et al., *J. Steroid Biochem.* 20:A33 No. 1381 (1984).
Rivier, *J. Ster. Bio.*, 20:A2 No. 1365 (1984).
Labrie, et al., *J. Steroid Biochem.* 28:379–384 (1987).
Labrie, et al., *The Prostate*, 4:579–584 (1983).
Lamb, *Am. J. Sports Medicine* 12:31–38 (1984).
Lambert, et al., *Ann. Clin. Biochem.* 23,225–229 (1986).
Lippman, et al., *Cancer Res.* 36:4610–4618 (1976).
Lippman, et al., *Cancer* 38:868–874 (1976).
Luthy, et al., *J. Steroid Biochem.* 31:845–852 (1988).
Maass, et al., *J. Steroid Biochem.* 6:743–749 (1975).
Manni, et al., *Cancer* 48:2507–2509 (1981).
Manni, et al., *Endocr. Rev.* 7:89–94 (1986).
Mouridsen, et al., *Cancer Treatm. Rev.* 5:131–141 (1978).
Nathanson, et al., *Rec. Prog. Horm. Res.* 1:261–291 (1947).
Nestor, Jr., et al., (1984) J. Steroid Biochem., 20 (6B), 1366.
Nicholson, et al., *Brit. J. Cancer* 39:268–273 (1979).
Nicholson, et al., *J. Ster. Biochem.* 23:843–848 (1985).
Plante, et al., *J. Steroid Biochem.* 31:61–64 (1988).
Potts, et al., *Steroids* 32:257–267 (1978).
Poulin, et al., *Breast Cancer Res. Treatm.* 12:213–225 (1989).

(List continued on next page.)

*Primary Examiner*—Kimberly Jordan
*Attorney, Agent, or Firm*—Ostrolenk, Faber, Gerb & Soffen, LLP

[57] ABSTRACT

A method of treatment of breast and endometrial cancer in susceptible warm-blooded animals may include inhibition of ovarian hormonal secretion by surgical (ovariectomy) or chemical (use of an LHRH agonist, e.g. [D-Trp⁶, des-Gly-NH₂¹⁰]LHRH ethylamide or antagonist) as part of a combination therapy comprising administering an antiestrogen together with at least one compound selected from the group consisting of an androgen, a progestin, at least one inhibitor of sex steroid formation, especially 17β-hydroxysteroid dehydrogenase and aromatase activity, at least one inhibitor of prolactin secretion, one inhibitor of growth hormone secretion and one inhibitor of ACTH secretion. Pharmaceutical compositions useful for such treatment and pharmaceutical kits containing such composition are disclosed.

46 Claims, 1 Drawing Sheet

OTHER PUBLICATIONS

Poyet, et al., *The Prostate* 9:237–246 (1986).
Raynaud, et al., *Mechanisms of Steroid Action* 145–158 (1981).
Raynaud, et al., *J. Steroid Biochem* 25:811–833 (1986).
Raynaud, et al., *Innovative Approaches in Drug Res.*, 47–72 (1986).
Raynaud, et al., *J. Steroid Biochem* 12:143–157 (1980).
Redding, et al., *Proc. Natl. Acad. Sci. USA* 80:1459–1462 (1983).
Robinson, et al., *J. Steroid Biochem.* 21:601–605 (1984).
Sandberg, et al., *Pharmac. Ther.* 36:263–307 (1988).
Schally, et al., *Cancer Treatment Reports* 68(1):281–289 (1984).
Stewart, et al., *Solid Phase Peptide Sythesis* (1969).
Taylor, *J. Endocr.*, 113:489–493 (1987).
Teulings, et al., *Cancer Res.* 40:2557–2561 (1980).
Thomas, et al., *J. Biol. Chem.* 258(3):1587–1590 (1983).
Thomas, et al., *J. Biol. Chem.* 258:11500–11503 (1983).
Van Veelen, et al., *Cancer* 58:7–13 (1986).
Vicens, et al., *Expansion Scientifique* 2:2139–2158 (1988).
Williams, et al., *Cancer Treatment Reports*, 71(12):1197–1201 (1987).
Poulin, Androgen and glucocorticoid receptor–mediated inhibition . . . , *Breast Cancer Res. Treatm.* 13:161–172 (1989).
Poulin, Inhibition of estrogen–dependent cell proliferation . . . , *Breast Cancer Res. Treatm.* 13:265–276 (1989).
Coombes, et al., *Br. J. Cancer* 46(1):30–4 (1982).
Neumannova, et al., *Obstet. Gynecol.* 66(5):695–700 (1985).
Robel, et al., *Prog. Clin. Bio. Res.* 142(Horm. Cancer):167–79 (1984).
Fukutomi, et al., *Jpn. J. Cancer Res.* (GANN) 77(1):92–7 (1986).
Grenman, et al., *Gynecol. Oncol.* 30(2):239–50 (1988).
Ishikawa, et al., *Horumon to Rinsho* 35(12):1359–66 (1987).
Tominaga, et al., *Jpn. J. Cancer Res.* (GANN) 76(11):1120–5 (1985).Chemical Abstracts, vol. 104, No. 62317h, Mar. 20, 1986.
Chemical Abstracts, vol. 104, No. 142440h, May 22, 1986.
Chemical Abstracts, vol. 108, No. 198573d, Jun. 27, 1988.
Chemical Abstracts, vol. 109, No. 32346c, Sep. 1, 1988.
Davidson and Lippman, *Oncogenesis* 1: 89–111, 1989.
Tormey et al., *Cancer Treatm. Rep.*, 60: 1451–1459, 1976.
Wynder, et al., *Cancer*, 19: 489–520, 1966.
Ayoub, et al., *Gynecol. Oncol.* 31(2):327–337 (1988).
Buzdar, et al., *Cancer* 50:1708–1712 (1982).
Cavalli, et al., *J. Clin. Oncol.* 2:414 (1984).
Covey, et al., *Endocrinology* 108:1597–1599 (1981).
Coy, et al., (1982) *Endocrinology* 110:1445–1447.
Gompel, et al., *J. Clin. Endo. Metab.* 63:1174–1180 (1986).
Harvey, et al., *LHRH and its Analogs* (1984).
Huggins, et al., *Cancer Res.* 12:134–141 (1952).
Johnson, et al., *Brit. J. Cancer* 50:363 (1984).
Johnston, et al., *Endocrinology* 115:776–785 (1984).
Klijn, et al., *Lancet* 1:1213–1216 (1982).
Labrie, et al., *Fertil. Steril.* 31:29–34 (1979).
Luthy, et al., *J. Gynecol. Endo.* 1:151–158 (1987).
Manni, et al., *J. Natl. Cancer Inst.* 74:941–944 (1985).
Minton, *Cancer* 33:358–363 (1974).
Robustelli della Cuna, Farmitalia Carlo Erba, S.P.A. (1987).
Welch, et al., *Cancer Res.* 30:1024–029 (1970).
Poulin, et al. "Stimulation of Cell Proliferation and Estrogenic Response by Adrenal $C_{19}$–$\Delta^5$–Steroids in the ZR–75–1 Human Breast Cancer Cell Line$_1$", *Cancer Research*, 46:4933–4937 (1986).
Tormey, et al., "Evaluation of Tamoxifen Doeses With and Without Fluoxymesterone in Advanced Breast Cancer", *Annals of Internal Medicine*, vol. 98, No. 2, pp. 139–144 (1983).
Dialog, Cancerlit Abstract No. 88744134 (1988).
A. Manni, et al., Cancer Research, Jun. 10, 1987, vol. 37, No. 4, pp. 1216–1219.
Annu. Meet. Am. Assoc. Cancer Research, 29:A930, 1988–Jun. 30, 1988.
F. Pannuti, et al., Panminerva Medica, 1981, Vo. 23, No. 3, pp. 157–160.
Chemical Abstracts, vol. 97, No. 85558p, Nov. 4, 1992.
Chemical Abstracts, vol. 100, No. 203835g, Aug. 23, 1984.
Chemical Abstracts, vol. 104, No. 998x, Jan. 30, 1986.
International Search Report on PCT/CA 90/00076.
CA 103:134186, Santen et al. (1984).
Hadley, Endocrinology [1984 Prentice–Hall Englewood, New Jersey], p. 463.

COMBINATION THERAPY FOR THE TREATMENT OF ESTROGEN-SENSITIVE DISEASE

This is a continuation of application Ser. No. 07/321,926 filed on Mar. 10, 1989, now abandoned.

BACKGROUND OF THE INVENTION

This invention relates to a method of treatment of breast and endometrial cancer in susceptible warm-blooded animals including humans and in particular to combination therapy involving administration of anti-estrogens in combination with other inhibitors of hormone production, inhibitors of hormone functions and/or in combination with other hormones.

Various investigators have been studying hormone-dependent breast and endometrial cancer. A known form of endocrine therapy in premenopausal women is castration most commonly performed by surgery or irradiation, two procedures giving irreversible castration. Recently, a reversible form of castration has been achieved by utilizing Luteinizing Hormone Releasing Hormone agonists ("LHRH agonists") which, following inhibition of secretion of bioactive Luteinizing Hormone ("LH") by the pituitary gland, decrease serum estrogens to castrated levels (Nicholson et al., Brit. J. Cancer 39, 268–273, 1979).

Several studies show that treatment of premenopausal breast cancer patients with LHRH agonists induces responses comparable to those achieved with other forms of castration (Klijn et al., J. Steroid Biochem. 20 1381, 1984; Manni et al., Endocr. Rev. 7: 89–94; 1986). Beneficial effects of treatment with LHRH agonist have also been observed in post-menopausal women (Nicholson et al., J. Ster. Biochem. 23, 843–848, 1985).

A. V. Schally et al., Cancer Treatment Reports, 68 (No. 1) 281–289 (1984), summarize the results of animal and clinical studies on growth inhibition of hormone-dependent mammary and prostate tumors by use of analogues of luteinizing hormone-releasing hormone, the so-called LHRH agonists and suggest that LHRH analogs and/or antagonists may have potential for treating breast cancer.

T. W. Redding and A. V. Schally, Proc. Natl. Acad. Sci. U.S.A. 80, 1459–1462 (1983) disclose reduction of estrogen-dependent memory tumors in rats and mice by use of an LHRH agonist (D-Trp$^6$]LHRH or of two specific antagonists.

In U.S. Pat. No. 4,071,622, it is disclosed that use of certain LHRH agonists causes regression of DMBA-induced mammary carcinoma in rats.

U.S. Pat. No. 4,775,660 relates to the treatment of female breast cancer by use of a combination therapy comprising administering an antiandrogen and an antiestrogen to a female after the hormone output of her ovaries has been blocked by chemical or surgical means.

U.S. Pat. No. 4,775,661 relates to the treatment of female breast cancer by use of a therapy comprising administering to a female after the hormone output of her ovaries has been blocked by chemical or surgical means an antiandrogen and optionally an inhibitor of sex steroid biosynthesis.

U.S. Pat. No. 4,760,053 describes a treatment of selected sex steroid dependent cancers which combines an LHRH agonist and/or an antiandrogen and/or an antiestrogen and/or at least one inhibitor of sex steroid biosynthesis.

In U.S. Pat. No. 4,472,382, it is disclosed that prostatic adenocarcinoma, benign prostatic hypertrophy and hormone-dependent mammary tumors may be treated with various LH-RH agonists and that prostrate adenocarcinoma and benign hypertrophy may be treated by use of various LHRH agonists and an antiandrogen. However, there is no suggestion or disclosure of the present invention.

Some clinical improvement in premenopausal women with breast cancer by use of the two LHRH agonists, Buserelin and Leuprolide, is also reported by H. A. Harvey et al. "LH-RH analogs in the treatment of human breast cancer", LHRH and its Analogs—A new Class of contraceptive and therapeutic Agents (B. H. Vickery and J. J. Nestor, Jr., and E. S. E. Hafez, eds) Lancaster, MTP Press, (1984) and the J. G. M. Klijn et al, "Treatment with luteinizing hormone-relating hormone analogue (Buserelin) in premenopausal patients with metastatic breast cancer", Lancet 1, 1213–1216 (1982).

Androgen receptors have been demonstrated in human breast cancer samples (Engelsman et al., Brit. J. Cancer 30, 177, 1975; Lippman et al., Cancer 38, 868–874, 1976; Maass et al., J. Steroid Biochem. 6, 743–749, 1975) and in human breast cancer cell lines including MCF-7 cells (Lippman et al., Cancer Res. 36, 4610–4618, 1976). Recent reports have indicated that androgen receptors may add to the selective power of estrogen receptors (ER) or even supplant ER towards predicting response to endocrine therapy (Bryan et al., Cancer 54, 2436–2440, 1984; Teulings et al., Cancer Res. 40: 2557–2561, 1980).

The first androgen successfully used in the treatment of advanced breast cancer is testosterone propionate (Nathanson, Rec. Progr. Horm. Res. 1, 261–291, 1947). Many studies subsequently confirmed the beneficial effect of androgens on breast cancer (Adair, Surg. Gynecol. Obstet. 84, 719–722, 1947; Alan and Herrman, Ann. Surg. 123, 1023–1035, 1946; Adair et al., JAMA 140, 1193–2000, 1949). These initial results stimulated cooperative studies on the effect of testosterone propionate and DES which were both found to be effective in producing objective remissions. (Subcommittee on Steroids and Cancer of the Committee on Research of the Council on Pharmacy and Chemistry of the Am. Med. Association followed by the Cooperative Breast Cancer Group under the Cancer Chemotherapy National Service Center of the NCI who found that testosterone propionate improved remission rate and duration, quality of life and survival (Cooperative Breast Cancer Group, JAMA 188, 1069–1072, 1964).

A response rate of 48% (13 of 27 patients) was observed in postmenopausal women who received the long-acting androgen methonolone enanthate (Kennedy et al., Cancer 21, 197–201, 1967). The median duration of survival was four times longer in the responders as compared to the non-responder group (27 versus 7.5 months). A large number of studies have demonstrated that androgen induce remission in 20 to 40% of women with metastatic breast cancer (Kennedy, Hormone Therapy in Cancer. Geriatrics 25, 106–112, 1970; Goldenberg et al., JAMA 223, 1267–1268, 1973).

The combination Fluoxymesterone and Tamoxifen has been shown to be superior to Tamoxifen alone. In fact, complete responses (CR) were seen only in the combination arm while 32% showed partial response (PR) in the combination arm versus only 15% in the monotherapy arm. In addition, there were only 25% non-responders in the combination therapy arm versus 50% in the patients who received TAM alone (Tormey et al., Ann. Int. Med. 98, 139–144, 1983). Moreover, the median time from onset of therapy to treatment failure was longer with Fluoxymesterone+Tamoxifen (180 days) compared to the Tamoxifen arm alone (64 days). There was a tendency for improved survival in the combination therapy arm (380 versus 330 days).

The independent beneficial effect of an antiestrogen combined with an androgen is suggested by the report that patients who did not respond to Tamoxifen could respond to Fluoxymesterone and vice versa. Moreover, patients treated with Tamoxifen and crossing over to Fluoxymesterone survived longer than the reverse regimen (Tormey et al., Ann. Int. Med. 98, 139–144, 1983). Recent in vitro studies compose the relative anti-proliferative activities of an anti-estrogen and an androgen on the growth of the estrogen-sensitive human mammary carcinoma cell line ZR-75-1 (Poulin et al. "Androgens inhibit basal and estrogen-induced cell proliferation in the ZR-75-1 human breast cancer cell line", Breast Cancer Res. Treatm. 12, 213–225, 1989a).

A response rate of 39% with an average duration of 11 months has recently been observed in a group of 33 postmenopausal women who previously failed or did not respond to Tamoxifen (Manni et al., Cancer 48: 2507–2509, 1981) upon treatment with fluoxymesterone (Halostatin) (10 mg, b.i.d). Of these women, 17 has also undergone hypophysectomy. There was no difference in the response rate to Fluoxymesterone in patients who had previously responded to Tamoxifen and in those who had failed. Of the 17 patients who had failed to both Tamoxifen and hypophysectomy, 7 responded to Fluoxymesterone for an average duration of 10 months. Among these, two had not responded to either Tamoxifen and hypophysectomy.

Since testosterone propionate had beneficial effects in both pre- and postmenopausal women (Adair et al., J. Am. Med. Ass. 15: 1193–100; 1949), it indicates that in addition to inhibiting gonadotropin secretion, the androgen exerts a direct inhibitory effect on cancer growth.

As mentioned above, Poulin et al. (Breast Cancer Res. Treatm. 12, 213–225, 1989a) have found that the growth of ZR-75-1 human breast carcinoma cells is inhibited by androgens, the inhibitory effect of androgens being additive to that of an antiestrogen. The inhibitory effect of androgens on the growth of human breast carcinoma cells ZR-75-1 has also been observed in vivo in nude mice.

Many clinical trails have shown the benefits of medroxyprogesterone acetate ("MPA") in breast cancer therapy (Cavalli et al., J. Clin. Oncol. 2, 414, 1984; Van Veelen et al., Cancer 58, 713, 1986; Johnson et al., Brit. J. Cancer 50, 363, 1984; Rabustelli della Cuna, G. Comprehensive guide to the therapeutic use of medroxyprogesterone acetate in oncology, Famitalia Carlo Erba, S.P.A., 1987).

Poulin et al. "Androgen and glucocorticoid receptor-mediated inhibition of cell proliferation by medroxyprogesterone acetate in ZR-75-1 human breast cancer cells", Breast Cancer Res. Treatm. 1989b, in press) have recently found that the inhibitory effect of medroxyprogesterone acetate (MPA) on the growth of the human ZR-75-1 breast cancer cells is mainly due to the androgenic properties of the compound. The androgenic properties of MPA have been clearly demonstrated in other systems (Labrie, C. et al., J. Steroid Biochem. 28: 379–384, 1987; Luthy et al., J. Steroid Biochem. 31: 845–852, 1988; Plante et al., J. Steroid Biochem., 31, 61–64, 1988). Other synthetic progestins have also been shown to possess, in addition to their progesterone-like activity, various degrees of androgenic activity (Labrie et al., Fertil, Steril. 31, 29–34, 1979; Poyet and Labrie, The Prostate 9, 237–246, 1986; Labrie, C. et al., J. Steroid Biochem. 28: 379–384, 1987; Luthy et al., J. Steroid Biochem. 31: 845–852, 1988; Plants et al., J. Steroid Biochem. 31, 61–64, 1988).

Poulin et al. "Inhibition of estrogen-dependent cell proliferation by the synthetic progestin R5020 and antagonism of progestin action by insulin in ZR-75-1 human breast cancer cells", Breast Cancer Res. Treatm., 1989c, in press) have observed that 17,21-dimethyl-19-non- 4,9-pregnadiene-3,20-dione ("R5020, promegestone") and progesterone itself can inhibit the growth of the human breast cancer cell line ZR-75-1 by an action mediated by the progesterone receptor. R5020 has been found to inhibit the growth of normal human breast cancer cells in culture in the presence as well as in the absence of $E_2$ (Gompel et al., J. Clin. Endocrinol. Metab. 63, 1174–1180, 1986).

H. Mouridsen et al., Cancer Treatm. Rev. 5, 131–141, (1978), disclose that Tamoxifen, an antiestrogen, is effective in remission of advanced breast cancer in about 30% of the women patients treated.

J. G. M. Klijn et al., (J. Steroid Biochem., 20 (No. 6B), 1381 (1984), disclosed the combined use of the antiestrogen, Tamoxifen, and the LHRH agonist, Buserelin, for treatment of breast cancer is known but objective remission of such cancers remains low (35%).

Various steroids have been described as irreversible aromatase inhibitors, including 4-hydroxy-4-androstene-3,17-dione (Brodie et al., Steroids 38: 693–702, 1981; Covey and Hood, Cancer Res. 42; Suppl. 3327s–3333s, 1982), androsta-4,6-triene-3,17-dione (Covey and Hood, Endocrinology 108, 1597–1599, 1981), MDL 18962 (Johnston et al., Endocrinology 115, 776–785, 1984), SH 489 (Henderson et al., J. Steroid Biochem. 24, 303–306, 1986) and 6-methylenandrosta-1,4-diene-3,17-dione ("FCE 24304") (Giudici et al., J. Steroid Biochem. 30: 391–394, 1988).

Huggins and Bergenstal (Cancer Res. 12, 134–141, 1952) have observed that adrenalectomy could induce remission in breast cancer patients who had failed after castration. Treatment of advanced breast cancer with aminoglutethimide after therapy with the antiestrogen Tamoxifen is disclosed by A. V. Buzdar et al. Cancer 50, 1708–1712 (1982).

High doses of ketoconazole can inhibit 17α-hydroxylase and C17-20-lyase (Santen et al., J. Clin. Endocrinol. Metab. 57, 732–736, 1983) while 16-methylene estrone can inhibit the 17β-HSD step (Thomas et al., J. Biol. Chem. 258, 11500–11503, 1983).

Trilostane and epostane have been described as inhibitors of 3β-hydroxy-steroid dehydrogenase activity (Ernshaw et al., Clin. Endocrinol, 21, 13–21, 1984; Robinson et al., J. Steroid Biochem. 21, 601–605, 1984; Lambert et al., Ann. Clin. Biochem. 23, 225–229, 1986; Potts et al., Steroids 32, 257–267, 1978) and have been successfully used for the treatment of breast cancer in combination with corticosteroids (Beardwell et al., Cancer Chemother. Pharmacol. 10: 158–160, 1983; Williams et al., Cancer Treat. Rep. 71, 1197–1201, 1987).

4-MA, (17β-N,N-diethylcarbamoyl-4-methyl-4-aza-5α-androstan-3-one) has been found to inhibit 3β-hydroxysteroid dehydrogenase activity in granulosa cells (Chan et al., Biochem. Biophys. Res. Commun. 144, 166–171, 1987). Epostane has been shown to inhibit 3β-hydroxysteroid dehydrogenase activity in pregnant goats (Taylor, J. Endocrinol. 113, 489–493, 1987).

A synthetic androgen, methyltrienolone has been reported to inhibit the growth of endometrial carcinoma cells in culture (Centola, Cancer Res. 45: 6264–6267, 1985). Medroxyprogesterone acetate is successfully used for the treatment of endometrial cancer (Ayoub et al., Gynecol. Oncol. 31(2): 327–337, 1988).

Prolactin and growth hormone have been shown to stimulate colony formation of the NMU rat mammary tumor cultured in vitro in the soft agar clonogenic assay (Manni and Wright, J. Natl Cancer Inst. 74, 941–944, 1985).

Prolactin is known to play a role in stimulating carcinoma in experimental animals, especially mammary carcinoma induced in the rate by dimethylbenz(a)anthracene (DMBA) (Welch et al., Cancer Res. 30, 1024–1029 1970). A study of 30 women suffering from breast cancer showed that 10 became pain-free upon treatment with L-Dopa, an inhibitor of prolactin secretion (Minton, Cancer 33, 358–363, 1974). In these 10 women, there were objective and subjective signs of tumor control.

A problem with prior art treatments is a lack of effective simultaneous control of both beneficial and detrimental hormones. Moreover, effective control of detrimental hormones (i.e. those hormones which may stimulate tumor growth) often requires closing down a plurality of pathways. Prior art treatments have tended to foreclose only particular synthetic pathways, leaving other pathways available for formation of the undesired hormone. Other treatments have attempted to block the activity of detrimental hormones such as estrogens. However, because such blocking is difficult to completely achieve, the formation of the estrogens, together with incomplete blocking, enables some estrogens to bind and undesirably activate receptors. This necessarily diminishes the effectiveness of treatment.

SUMMARY OF THE INVENTION

It is an object of the present invention to provide combination therapy for the treatment of breast cancer and endometrial cancer wherein the treatment selectively inhibits the formation and/or action of hormones which would otherwise contribute to tumor growth, while maintaining those which do not increase growth and are otherwise beneficial to general health.

It is another object of the invention to provide combination therapy having increased effectiveness in slowing or reversing tumor growth.

It is another object of the invention to provide therapy for treating breast or endometrial cancer having significantly reduced frequency of unwanted side effects.

It is a further object of the invention to provide kits having a combination of pharmaceutical compositions which may be effectively utilized together for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

These and other objects are achieved by providing a method of treating breast or endometrial cancer in a warm-blooded animal wherein said method comprises inhibiting the ovarian hormonal secretions of said animal and administering to said animal therapeutically effective amounts of an antiestrogen and at least one compound selected from the group consisting of an androgen, a progestin, an inhibitor of sex steroid formation, an inhibitor of prolactin secretion, an inhibitor of growth hormone secretion and an inhibitor of ACTH secretion.

The invention further provides a method for treating breast or endometrial cancer in a warm-blooded animal in need of such treatment which comprises administering to such animals a therapeutically effective amount of an antiestrogen and at least one compound selected from the group consisting of an inhibitor of sex steroid formation, an inhibitor of prolactin secretion, an inhibitor of growth hormone secretion, an inhibitor of adrenal corticotrophin hormone secretion and a progestin.

The invention further provides a kit for treatment of breast or endometrial cancer, said kit including a pharmaceutical composition comprising an antiestrogen and at least one pharmaceutical composition selected from the group consisting of a pharmaceutical composition comprising a progestin, a pharmaceutical composition comprising an inhibitor of sex steroid formation, a pharmaceutical composition comprising an inhibitor of prolactin secretion, a pharmaceutical composition comprising an inhibitor of ACTH secretion and a pharmaceutical composition comprising an inhibitor of growth hormone secretion.

The invention further provides a therapeutic composition for treating breast or endometrial cancer in a warm-blooded animal which comprises an ovarian secretion inhibitor, an antiestrogen, and at least one compound selected from the group consisting of an androgen, a progestin, an inhibitor of sex steroid formation, an inhibitor of prolactin secretion, an inhibitor of growth hormone secretion and an inhibitor of ACTH secretion.

The invention contemplates that any of the active ingredients discussed herein may be utilized in combination with diluents and other carriers, for oral or parenteral administration, or may be delivered by any conventional delivery system. In certain preferred embodiments, active ingredients necessary to the combination therapy described above may be combined in a single pharmaceutical composition for simultaneous administration.

DETAILED DESCRIPTION OF THE PREFERRED EMBODIMENT

Figure 1:
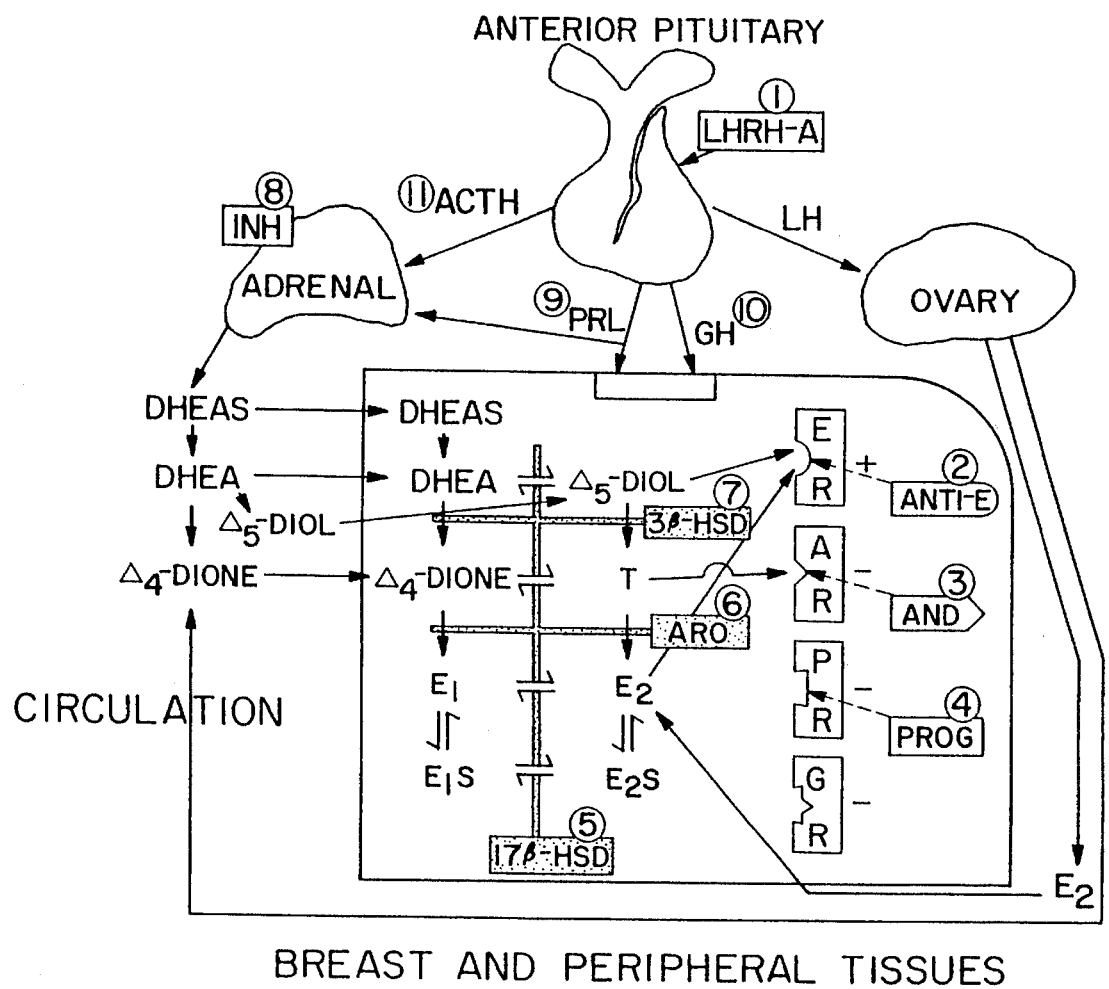
FIG. 1 is a schematic representation of the sites of action of drugs active in the treatment of breast cancer. The following abbreviations are used: ER: estrogen receptor; AR: androgen receptor; PR: progesterone receptor; GR: glucocorticoid receptor; DHEAS: dehydroepiandrosterone sulfate; DHEA: dehydroepiandrosterone; $\Delta^5$-diol androst-5-ene- 3$\beta$,17$\beta$-diol; $\Delta^4$-dione, androstenedione; $E_1$: estrone; $E_2$: 17$\beta$-estradiol; T: testosterone; DHT: dihydrotestosterone; $E_2S$: $E_2$-sulfate; $E_1$-S; $E_1$ sulfate; (1) LHRH-A; luteinizing hormone-releasing hormone agonist or antagonist; (2) ANTI-E: antiestrogen; (3) AND: androgen; (4) PROG: progestin; (5) 17$\beta$-HSD; inhibitor of 17$\beta$-estradiol steroid dehydrogenase or 17$\beta$-hydroxysteroid dehydrogenase; (6) ARO: inhibitor of aromatase activity; (7) 3$\beta$-HSD: inhibitor of 3$\beta$-hydroxysteroid, $\Delta^5$–$\Delta^4$ isomerase; (8) INH: inhibitor of adrenal steroidogenesis; (9) PRL: inhibitor of prolactin secretion; (10) GH: inhibitor of growth hormone secretion; (11) ACTH: inhibitor of ACTH secretion.

Referring to FIG. 1, the "+"s and "−"s next to each indicated receptor designate whether activation of that receptor aids or hinders tumor growth. As may be seen from FIG. 1, activation of the estrogen receptor will stimulate tumor growth, and is therefore to be prevented. However, it is important to continue to activate the androgen receptor, whose activation may inhibit tumor growth. Likewise, it is desirable to continue to activate the progesterone and glucocorticoid receptors.

One method of inhibiting activation of the estrogen receptor is treatment with an effective antiestrogen compound having an affinity for the receptor site such that it binds the receptor site and blocks estrogen from binding and activating the site. It is important to select antiestrogens which tend to be pure antagonists, and which have no agonistic activity. Otherwise, the antiestrogen which blocks the receptor site from estrogen, may itself activate the site. Preferred antiestrogens are discussed in detail below. Because it is extremely difficult to block all receptor sites, it is desirable to simultaneously decrease the concentration of estrogen available to activate estrogen receptors. Hence, it is desirable to inhibit production of estrogen by the ovaries. This may be accomplished in a variety of ways including surgical removal of the ovaries, irradiation of the ovaries, or by chemical means. Chemical means include but are not limited to the use of agonists or antagonists of luteinizing hormone releasing hormone. These compound act on the pituitary in a manner effective to stop its production of bioactive luteinizing hormone, a hormone necessary to cause the ovaries to produce and secrete estrogen and/or other hormones which may be converted to estrogen.

As may be seen from the scheme of FIG. 1, a number of hormones released by the adrenals may be converted by a variety of biological pathways into estrogen. Among the estrogens thus produced are 17β-estradiol and androst-5-ene-3β,17β-diol. It is therefore highly desirable to include an inhibitor of 17β-estradiol dehydrogenase or 17β-hydroxy steroid dehydrogenase. Such inhibitors close down the synthetic pathways crossed by vertical line 5 denoted "17β-HSD" on FIG. 1. Hence synthesis of both major forms of estrogen shown on FIG. 1 is substantially prevented. Other sex steroid formation inhibitors such as inhibitors of 3β-hydroxy steroid or of aromatase activity are also preferably included in treatment in order to close down the synthetic pathways crossed by the two horizontal lines 6 and 7 denoted "ARO" and "3β-HSD", respectively.

It will be noted that the foregoing methods of inhibiting estrogen synthesis also have the undesirable effect of inhibiting androgen synthesis. Because androgens are beneficial to retarding tumor growth, it is desirable to administer ("add block") androgens in connection with any of the foregoing treatments which inhibit sex steroid synthesis. Other preferred additions to treatment include progestins, inhibitors of growth hormone secretion, inhibitors of prolactin secretion and inhibitors of adrenal corticotrophin hormone secretion. The latter has the effect of preventing ACTH from reaching the adrenals and thus of preventing the adrenals from synthesizing and secreting compounds such as dehydroepiandrosterone sulfate, a precursor of the synthesis of estrogen. Alternatively, inhibitors which close down synthetic pathways in the adrenals will achieve the same result. When adrenal secretions are inhibited or stopped, essential glucocorticoids should be added back as part of the therapy.

In one embodiment, the invention provides a method of treating breast and endometrial cancer in a warm-blooded animal in need of such treatment which may comprise inhibiting the ovarian hormonal secretions of said animal by surgical, radiotherapeutical or chemical means and administering to said animal therapeutically effective amounts of an antiestrogen and at least one compound selected from the group consisting of an androgen, a progestin, at least one inhibitor of sex steroid formation, one inhibitor of prolactin secretion, one inhibitor of growth hormone and one inhibitor of ACTH secretion or mixtures thereof.

In certain embodiments, the invention provides a method of treating breast cancer which comprises administering a therapeutically effective amount (1) of an antiestrogen and a progestin, (2) of an antiestrogen and at least one inhibitor of sex steroid biosynthesis, (3) of an antiestrogen, an androgen and a progestin, (4) of an antiestrogen, an androgen and at least one inhibitor of sex steroid biosynthesis, (5) of an antiestrogen, a progestin and at least one inhibitor of sex steroid biosynthesis, (6) of an antiestrogen, an androgen, a progestin and at least one inhibitor of sex steroid biosynthesis, (7) of an antiestrogen, an androgen, and at least one inhibitor of prolactin secretion and/or growth hormone secretion and/or ACTH secretion, (8) an antiestrogen, a progestin and at least one inhibitor of prolactin secretion and/or growth hormone secretion and/or ACTH secretion, (9) an antiestrogen, at least one inhibitor of sex steroid formation and at least one inhibitor of prolactin secretion and/or growth hormone secretion and/or ACTH secretion, (10) an antiestrogen, an androgen, a progestin and at least one inhibitor of prolactin secretion and/or growth hormone secretion and/or ACTH secretion, (11) an antiestrogen, and androgen, at least one inhibitor of sex steroid formation and at least one inhibitor of prolactin secretion and/or growth hormone and/or ACTH secretion, (12) an antiestrogen, a progestin, at least one inhibitor of sex steroid formation and at least one inhibitor of prolactin secretion and/or growth hormone secretion and/or ACTH secretion, (13) an antiestrogen, an androgen, a progestin, at least one inhibitor of sex steroid formation and at least one inhibitor of prolactin secretion and/or growth hormone secretion and/or ACTH secretion.

In one aspect, the invention provides a method of treating breast or endometrial cancer in a warm-blooded female animal in need of such treatment which comprises administering to said animal whose hormone output of the ovaries is blocked, a therapeutically effective amount of an antiestrogen, an androgen and a blocker of steroid biosynthesis or a pharmaceutical composition thereof. The ovarian hormonal secretions of said animal can be blocked by surgical or chemical means. In one aspect, the invention provides a method of treating cancer in a castrated warm-blooded female animal (i.e., one whose ovaries are blocked by surgical or chemical means for secreting estrogen) which comprises administering an antiestrogen and an androgen or pharmaceutical compositions thereof, in amounts sufficient to treat such cancers.

In certain embodiments, the ovaries may be surgically removed (oophorectomy) but preferably the secretion of hormones from the ovaries is blocked chemically by administering an effective amount of an LHRH agonist or antagonist. In one preferred aspect, the present invention provides a method of treating breast and endometrial cancer in a warm-blooded animal, which comprises administering to an animal in need of such treatment an LHRH agonist or antagonist, an antiestrogen, an androgen, and at least one inhibitor of sex steroid formation, or pharmaceutical compositions thereof, in amounts sufficient to treat breast and endometrial cancer.

In its preferred aspect, the LHRH agonist is administered parenterally (subcutaneously or intramuscularly) and the androgen, antiestrogen, and at least one inhibitor of sex steroid formation are each administered orally. The invention also provides kits or single packages combining the preferred pharmaceutical compositions of the invention. For example, a three-component kit provides an LHRH agonist parenteral pharmaceutical composition, an androgen oral pharmaceutical composition and an antiestrogen oral composition. A four-component kit may provide, for example, an LHRH agonist parenteral pharmaceutical composition, an antiestrogen oral pharmaceutical composition, an androgen oral composition and a steroid biosynthesis inhibitor oral composition. In certain preferred embodiments, the antiestrogen itself also acts as a sex steroid inhibitor, and the kit need only contain one pharmaceutical composition for achieving both functions.

Thus, this invention provides a novel method for effective treatment of breast and endometrial cancer. In addition, the amounts of antiestrogen administered in this combined therapy are lower than normally used in the prior art, e.g., J. G. M. Klijn et al., J. Steroid Biochem. 20 (no. 6B) 1381 (1984), to treat breast cancer, and thus, the harmful effects of relatively large doses of antiestrogen are minimized.

By combining an optimal blockade of estrogen formation and/or action and the inhibitory effect of androgens on breast and endometrial cancer cell growth, the present invention provides a method of maximally inhibiting the growth of breast and endometrial cancer.

In female mammals, the ovaries may be surgically removed (oophorectomy) or irradiated. However, it is preferred that secretion of estrogens from the ovaries be blocked by chemical castration, for example, by administering an effective amount of an LHRH agonist or antagonist.

In its preferred aspect, the LHRH agonist is administered parenterally (subcutaneously or intramuscularly or intranasally) and, in association therewith, the antiestrogen, and androgen and the inhibitor of sex steroid biosynthesis are each administered orally. Thus, this invention provides a novel method for effective treatment of breast and endometrial cancer. In another preferred aspect, the antiestrogen, androgen and/or inhibitor of sex steroid biosynthesis are administered in a controlled release formation.

In one preferred aspect, the present invention provides an effective method of treating breast and endometrial cancer in warm-blooded female animals in need of such treatment by administering an LHRH agonist or antagonist, in association with an antiestrogen, a progestin, an androgen and an inhibitor of sex steroid biosynthesis or pharmaceutical compositions thereof in amounts sufficient to inhibit tumor growth. These active compounds can be administered together or an any order as discussed hereinafter.

To assist in determining the effect of the treatment, blood plasma concentrations of the sex steroids of adrenal and ovarian origin, i.e., precursor steroids, androgens and estrogens, and tumor size are measured. Lowered concentrations of sex steroids and reduction in tumor size are indicative of successful treatment, e.g. inhibition of tumor growth using active compounds described herein in accordance with the present invention. The concentrations of adrenal androgens and estrogens such as dehydroepiandrosterone (DHEA), DHEA-S sulfate (DHEAS), androst-5-ene-3β,17β-diol (Δ'-diol) and, the ovarian estrogen, 17β-estradiol ($E_2$) are measured by standard methods well known to those skilled in the art, see for example, F. Labrie et al., The Prostate 4, 579–584, 1983; Luthy et al., J. Gynecol. Endocrinol., 1, 151–158, 1987).

The change in tumor size is measured by standard physical methods well known to those skilled in the art, e.g., bone scan, chest X-ray, skeletal survey, ultrasonography of the liver and the liver scan (if needed), CAT-scan and physical examination.

While a LHRH agonist or a LHRH antagonist may be used in one preferred aspect of the present invention, the use of a LHRH agonist is more preferred.

By the term "LHRH agonist" is meant synthetic analogues of the natural luteinizing hormone-releasing hormone (LHRH), for example, a decapeptide of the structure: L-pyroglutamyl-L-histidyl-L-tryptophyl-L-seryl-L-tyrosyl-glycyl-L-leucyl-L-arginyl-L-propylglycyl-$NH_2$. Suitable LHRH agonists include nonapeptides and decapeptides represented by the formula: L-pyroglutamyl-L-histidyl-L-tryptophyl-L-seryl-L-tyrosyl-X-Y-arginyl-L-prolyl-Z wherein X is D-tryptophyl, D-leucyl, D-alanyl, iminobenzyl-D-histidyl, 3-(2-naphthyl)-D-alanyl, O-tert-butyl-D-seryl, D-tyrosyl, D-lysyl, D-phenylalanyl or N-methyl-D-alanyl and Y is L-leucyl, D-leucyl, $N^\alpha$-methyl D-leucyl, $N^\alpha$-methyl-L-leucyl or D-alanyl and wherein Z is glycyl-$NHR_1$ or $NHR_1$ wherein $R_1$ is H, lower alkyl or lower haloalkyl. Lower alkyl includes straight- or branched-chain alkyls having 1 to 6 carbon atoms, e.g., methyl, ethyl, propyl, pentyl or hexyl, isobutyl, neopentyl and the like. Lower haloalkyl includes straight- and branched-chain alkyls of 1 to 6 carbon atoms having a halogen substituent, e.g., $-CF_3$, $-CH_2CF_3$, $-CF_2CH_3$. Halogen means F, Cl, Br, I with Cl being preferred.

In preferred nonapeptides, Y is L-leucyl, X is an optically active D-form of tryptophan, serine (t-BuO), leucine, histidine (iminobenzyl), and alanine.

Preferred decapeptides include [D-Trp$^6$]-LHRH wherein X-D-Trp, Y-L-leucyl, Z-glycyl-$NH_2$, [D-Phe$^6$]LHRH wherein X-D-phenylalanyl, Y-L-leucyl and Z-glycyl-$HN_3$) or [D-Nal(2)$^6$]LHRH which is [(3-(2-naphthyl)-D-Ala$^6$]LHRH wherein X-3-(2-naphthyl)-D-alanyl, Y-L-leucyl and Z-glycyl-$NH_3$).

Other LHRH agonists useful within the scope of this invention are the α-aza analogues of the natural LH-RH, especially, [D-Phe$^6$, Azgly$^{10}$]-LHRH, [D-Tyr(Me)$^6$, Azgly$^{10}$]-LHRH, and [D-Ser-(t-BuO)$^6$, Azgly$^{10}$]-LHRH, disclosed by A. S. Dutta et al. in J. Med. Chem., 21, 1018 (1978) and U.S. Pat. No. 4,100,274 as well as those disclosed in U.S. Pat. Nos. 4,024,248 and 4,118,483.

Typical suitable LHRH antagonists include [N-Ac-D-p-Cl-Phe$^{1,3}$,D-Phe$^3$, D-Arg$^6$, D-Ala$^{10}$]LHRH disclosed by J. Ercheggi et al., Biochem. Biophys. Res. Commun. 100, 915–920, (1981); [N-Ac-D-p-Cl-Phe$^{1,2}$, D-Trp$^3$, D-Arg$^6$, D-Ala$^{10}$]LHRH disclosed by D. H. Coy et al., Endocrinology, 110: 1445–1447, (1982); [N-Ac-D-(3-(2-naphthyl)-Ala)$^1$, D-p-Cl-Phe$^2$, D-Trp$^3$, D-hArg(Et$_2$)$^6$, D-Ala$^{10}$]-LHRH and [N-Ac-Pro$^1$, D-p-F-Phe$^2$, (D-(3-(2-naphthyl)Ala $^{3,6}$]-LHRH disclosed by J. J. Nestor et al. J. Steroid Biochem., 20 (No. 6B), 1366 (1984); the nona- and decapeptides analogs of LHRH useful as LHRH antagonists disclosed in U.S. Pat. No. 4,481,190 (J. J. Nestor et al.); analogs of the highly constrained cyclic antagonist, cycle [Δ$^3$Pro$^1$, D-p-Cl-Phe$^2$, D-Trp$^{3,5}$, N-Me-Leu$^7$, β-Ala$^{10}$]LHRH disclosed by J. Rivier, J. Steroid Biochem., 20, (No. 6B), 1365 (1984), and [N-Ac-D-(3-(2-naphthyl)-Ala)$^1$, D-p-F-Phe$^2$, D-Trp$^3$, D-Arg$^6$]-LHRH disclosed by A. Corbin et al., J. Steroid Biochem. 20 (No. 6B) 1369 (1984).

Other LHRH agonist and antagonist analogs are disclosed in LHRH and its Analogues (B. H. Vickery et al. editors at page 3–10 (J. J. Nestor), 11–22 (J. Rivier et al.) and 23–33 (J. J. Nestor et al.).

The LHRH agonists and antagonists useful in this invention may conveniently be prepared by the method described by Stewart et al. in "Solid Phase Peptide Synthesis" (published in 1969 by Freeman & Co., San Francisco, page 1) but solution synthesis may also be used.

The nona- and decapeptides used in this invention are conveniently assembled on a solid resin support, such as 1% cross-linked Pro-Merrifield resin by use of an automatic peptide synthesizer. Typically, side-chain protecting groups, well known to those in the peptide arts, are used during the dicyclohexylcarbodiimide-catalyzed coupling of a tert-butyoxycarbonylamino acid to the growing peptide attached to a benzhydrylamine resin. The tert-butyloxycarbonyl protecting groups are removed at each stage with trifluoracetic acid. The nona- or decapeptide is cleaved from the resin and deprotected by use of HF. The crude peptide is purified by the usual techniques, e.g., gel filtration, HPLC and partition chromatography and optionally lyophilization. See also D. H. Coy et al., J. Med. Chem. 19, pages 423–452, (1976).

Typically suitable androgens include 6-alpha-methyl,17-alpha-acetoxy progesterone or medroxyprogesterone acetate available, among others, from Upjohn and Farmitalia Carlo Erba, S.p.A. under the trade names, among others, of Provera and Farlutal, and the acronym MPA.

Other suitable androgens include other synthetic progestins as described in Labria et al. (Fertil. Steril. 31: 29–34, 1979) as well as anabolic steroids or "progestins" (Raynaud and Ojasoo, in: Innovative Approaches in Drug Research. Elsevier Sc. Publishers, Amsterdam, pp. 47–72, 1986; Sandberg and Kirdoni, Pharmac. Ther. 36: 263–307, 1988; and Vincens, Simard and De Lignières, Les Androgènes. In: Pharmacologie Clinique, Base de Thérapeutique, 2i ème èdition, Expansion Scientifique (Paris), pp. 2139–2158, 1988), as well as Calusterone (7β,17α-dimethyl-testosterone), anabolic steroids (Lamb, Am. J. Sports Medicine 12, 31–38, 1984; Hilf, R. Anabolic-androgenic steroids and experimental tumors. In: (Kochachian, C. D., ed.), Handbook of Experimental Pharmacology, vol. 43, Anabolic-Androgenic Steroids, Springer-Verlag, Berlin, 725 pp., 1976), fluoxymesterone (9α-fluoro-11β-hydroxy-17α-methyl testosterone), testosterone 17β-cypionate, 17α-methyltestosterone, Pantestone (testosterone undecanoate), $\Delta^1$-testololactone and Andractim.

Typically suitable progestins include 17,21-dimethyl-19-nor-4,9-pregnadiene- 3,20-dione ("R5020, promegestone") available from Roussel-UCLAF as well as cyproterone acetate (Androcur) available from Schering Ag. 6-alpha-methyl, 17-alpha-acetoxy progesterone or medroxyprogesterone acetate (MPA) available from, among others, Upjohn and Farmitalia, Calbo Erba, Gestoden available from Shering, magestrol acetate (17α-acetoxy-6-methyl-pregna-4,6-diene- 3,20-dione) available from Mead Johnson & Co., Evansville, Ind., under the trade name of Megace. Other progestins include Levolorgestrel, Gestodene, desogestrel, 3-keto-desogestrel, norethindrone, norethisterone, 13α-ethyl-17-hydroxy-18,19-dinor-17β-pregna- 4,9,11-triene-20-yl-3-one (R2323), demegestone, norgestrienone, gastrinone, progesterone itself and others described in Raynaud and Ojasoo, J. Steroid Biochem. 25: 811–833, 1986; Raynaud et al., J. Steroid Biochem. 12: 143–157, 1980; Raynaud, Ojasoo and Labrie, Steroid Hormones, Agonists and Antagonists, In: Mechanisms of Steroid Action (G. P. Lewis and M. Ginsburg, eds), McMillan Press, London, pp. 145–158 (1981).

Typical suitable antiestrogens include those steroidal and non-steroidal antiestrogens such as (1RS,2RS)-4,4'-diacetoxy-5,5'-difluoro-(1-ethyl- 2-methylene)di-m-phenylenediacetate, which is available from Biorex under the trade name of Acefluranol, 6α-chloro-16α-methyl-pregn-4-ene-3,20-dione which is available from Eli Lilly & Co., Indianapolis, Ind. under the trade name of Clometherone, 6-chloro-17-hydroxypregna-1,4,6-triene- 3,20-dione which is available as the acetate salt from Syntex Labs, Palo Alto, Cal. as Delmadione Acetate, 17-hydroxy-6-methyl-19-norpregna- 4,6-diene-3,20-dione which is available from Theramex under the name of Lutenyl, 1-[2-[4-[1-(4-methoxyphenyl)-2-nitro-2-phenylethenyl)phenoxy]ethyl]-pyrrolidine which is available as the citrate salt from Parke-Davis Div. of Warner-Lambert Co., Morris Plains, N.J. under the name of Nitromifene Citrate, substituted aminoalkoxyphenylalkenes such as (Z)-2-[4-(1,2-diphenyl-1-butenyl)-phenoxy]-N,N-dimethylethanamine which is available as the citrate salt from Stuart Pharmaceuticals, Wilmington, Del, as Tamoxifen Citrate (see also Belgian patent No. 637,389, Mar. 1964), 3,4-dihydro-2-(p-methoxyphenyl)-1-naphthyl p-[2-(1-pyrrolidinyl)ethoxy]phenyl ketone which is available as the methane sulfonate salt from Eli Lilly & Co. under the tradename of Trioxifene Mesylate, 1-[4'-(2-phenyl)-bl-(3'-hydroxyphenyl)-2-phenyl-but-1-ene which is available from Klinge Pharma, [6-hydroxy-2-(p-hydroxyphenyl)-benzo(b-)thien- 3yl]-[2-(1-pyrrolidinyl)-ethoxy phenyl]ketone which is available from Eli Lilly & Co. (LY 117018), [6-hydroxy-2-(4-hydroxyphenyl)benzo(b)thien- 3-yl]-[4-(2-(1-piperdinyl)ethoxy)phenyl]methanone, which is available from Eli Lilly & Co. as the hydrogen chloride salt (LY156758) and meso-3,4-bis(3'-hydroxyphenyl) hexane as well as the dimethyl, dipropyl and 3'-acetoxy phenyl analogues which are described in U.S. Pat. No. 4,094,994 and a series of 1-phenyl-alkane and -alkenes, e.g. (E)-3-cyclopentyl-1-(4-hydroxyphenyl)-1-phenyl-1-butene and 2-cyclo-pentyl- 1-[4-hydroxy or methoxyphenyl]-3-phenyl-2-propen-1-ol and FC-1157 which is available as the citrate salt from Farmos Group, Ltd., Turku, Finland (see also Eur. Pat. Appln. Ep. No 78,158). It is preferred to use an antiestrogen which shows minimal partial estrogen agonism. FC-1157, LY-117018, LY 156758 and Tamoxifen are at the preferred antiestrogens of the class of those possessing some agonistic activity.

Suitable antiestrogens which also include 7α-substituents of estradiol (European Pat. No. 0138504) and non-steroidal compounds bearing a similar aliphalic side-chain (U.S. Pat. No. 4,732,912) are represented by the general formula I:

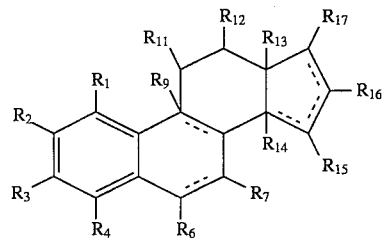

wherein the dotted lines represent optional double bonds;

wherein $R_1$, $R_2$ and $R_4$ are independently selected from the group consisting of hydrogen, hydroxyl, alkylsulfonyl(lower)alkoxy, arylsulfonyl(lower)alkoxy, halogen, lower alkyl, lower alkoxy, lower alkylsilyl, amino and nitro;

wherein $R_3$ is selected from the group consisting of hydrogen, hydroxyl, halogen, lower alkyl, methoxy, ethoxy, propoxy, hydroxyethoxy, lower alkoxy, acetoxy, propionyloxy, butyryloxy, oenanthoyloxy, cypionoyloxy, trans-4-n-butyl-cyclohexanecarbonoyloxy, $(C_2-C_{20})$alkanoyloxy, lower alkoxy carbonyloxy, carboxy, $(C_3-C_{20})$alkenoyloxy, $(C_3-C_{20})$alkanoyloxy or $(C_7-C_{10})$aroyloxy; wherein $R_6$ is selected from the group consisting of hydrogen, halogen, lower alkyl, amino and nitrile;

wherein $R_7$ is in a position and is hydrogen, hydroxy, halogen, lower alkyl, lower alkoxy, lower alkylsilyl, amino, nitrile, nitro, nitroso, alkylsulfonyl, arylsulfonyl, lower alkylamino, diloweralkylamino, or is represented by the formula $AXR_{21}$ and $A^1\text{-}[Y\text{-}A^{11}]_u\text{-}X\text{-}R_{31}$ wherein:

A is straight- or branched-chain $(C_2\text{-}C_{30})$alkylene, $(C_3\text{-}C_{30})$alkenylene, $(C_3\text{-}C_{30})$alkynylene or fluoro-substituted analogs of the foregoing; u is an integer from 0 to 5; wherein $A^1$ and $A^{21}$ may be the same or different and are selected from the group consisting of a bond, straight- or branched-chain alkylene, straight- or branched-chain alkynylene, straight- or branched-chain alkenylene, and fluoro-substituted analogs of the foregoing, wherein $A^1$ and $A^{11}$ together have a total of from 3 to 30 carbon atoms, and Y is selected from the group consisting of —O—, —S—, —Se—, —SO—, —SO$_2$—, —CO—, —NR$_{23}$—, —SiR$_{22}$R$_{22}$—, —CR$_{22}$OR$_{22}$—, —NR$_{22}$CO—, —NR$_{22}$CS—, —CONR$_{22}$—, —CSNR$_{22}$—, —COO—, —COS—, —SCO—, —CSS—, —SCS—, —OCO— and phenylene ($R_{22}$ being hydrogen or lower alkyl); $R_{21}$ is selected from the group consisting of hydrogen, straight- or branched-chain lower alkyl, lower alkenyl or lower alkynyl, $(C_3\text{-}C_7)$cycloalkyl, halogeno(lower)alkyl, carboxy(lower)alkyl, (lower)alkoxycarbonyl(lower)alkyl, $(C_5\text{-}C_{10})$aryl, $(C_7\text{-}C_{11})$arylalkyl, di(lower)alkylamino(lower)alkyl and fluoro-substituted analogs of the foregoing, and wherein X is —CONR$_{23}$—, —CSNR$_{22}$—, —NR$_{24}$CO—, —NR$_{24}$CS—, —NR$_{24}$CONR$_{23}$—,

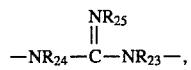

—SO$_2$NR$_{33}$—, —CSS—, —SCS—, —NR$_{23}$—, —(NO)R$_{23}$—, —(PO)R$_{23}$—, —NR$_{24}$COO—, —NR$_{24}$SO$_2$—, —S—, —SO— or —SO$_2$—, (where $R_{23}$ is selected from the group consisting of hydrogen, lower alkyl, and a species which, together with $R_{21}$, forms a saturated or unsaturated heterocyclic ring having at least one nitrogen atom and, optionally, a second heteroatom selected from the group consisting of oxygen, sulfur, silicon, selenium, nitrogen and fluoro-substituted analogs of the foregoing, and where $R_{24}$ is hydrogen or lower alkyl) wherein $R_{23}$ is hydrogen, nitrile or nitro) ($XR_{21}$ may form a tetrazole ring);

wherein $R_{11}$ is selected from the group consisting of hydrogen, lower alkyl, lower alkenyl, lower alkynyl, $(C_6\text{-}C_{10})$aryl, alkylsulfonyl, arylsulfonyl, a substituted 5- to 7-member heterocyclic ring having at least one heteroatom (selected from oxygen, sulfur, silicon, selenium, nitrogen), —(CH$_2$)$_8$W (wherein W is nitrile, hydroxyl, azido, nitroso, nitro, thionitrile, halogen, alkylsulfonyl or arylsulfonyl, and s is an integer from 1 to 6), OR$_{26}$ (wherein $R_{26}$ is hydrogen, lower alkyl or $(C_6\text{-}C_{10})$aryl), DR$_{27}$ (wherein D is —Se—, —NR$_{36}$, —S— or —O—, and $R_{27}$ is hydrogen, lower alkyl), =O, =S, =Se, =NR$_{28}$ (wherein $R_{28}$ is hydrogen or lower alkyl wherein $R_{12}$ and $R_{13}$ are independently hydrogen or lower alkyl;

wherein $R_{14}$ is selected from the group consisting of hydrogen, hydroxyl, nitrile, nitro, nitroso, halogen, lower alkyl, lower alkoxy, lower alkyseleno, lower alkylamino or diloweralkylamino; or $R_{14}$ and $R_{15}$ together are —CH$_2$—, —CHX—, —CX$_2$—, (X=halogen, carboxyl or alkoxycarbonyl), —O—, —S—, —Se—, >N—CN, >NR$_{39}$ and >NCO$_3$R$_{39}$ wherein $R_{23}$ is hydrogen or lower alkyl;

wherein $R_{15}$ is selected from the group consisting of hydrogen, hydroxyl, nitro, nitroso, halogen, lower alkyl, lower alkenyl, lower alkynyl, lower alkoxy, lower alkylseleno, lower alkylamino, di(lower)alkylamino, nitrile, azido, arylseleno, $AXR_{21}$, $A_1\text{—}[Y\text{—}A^{11}]_u\text{—}X\text{—}R_{21}$ or $R_{15}$ and $R_{16}$ together are —CH$_3$—, —CHX—, —CX$_2$—, (X=halogen, carboxyl or alkoxycarbonyl), —O—, —S—, —Se—, >N—CN, >NR$_{29}$ and >NCO$_2$R$_{29}$ wherein $R_{29}$ is hydrogen or lower alkyl;

wherein $R_{16}$ is selected from the group consisting of hydrogen, nitroso, halogen, lower alkyl, carboxyl, lower alkoxy, lower alkylselene, lower alkylamino, nitrile, azido, arylselene, lower alkylseleno, di(lower)alkylamino, $AXR_{21}$, or $A^1\text{—}[Y\text{—}A^{11}]_u\text{—}X\text{—}R_{21}$, wherein $R_{17(\alpha)}$ is selected from the group consisting of hydrogen, hydroxyl, lower alkyl, halogeno(lower)alkyl, $AXR_2$, $A^1\text{—}[Y\text{—}A^{11}]_uX\text{—}R_{21}$, $B^1\text{—}T\text{—}R_{20}$ wherein:

$B^1$ is straight- or branched-chain $(C_1\text{-}C_{12})$alkylene, $(C_2\text{-}C_{12})$alkynylene, $(C_3\text{-}C_{12})$alkenylene; T is —O—, —NR$_{31}$, —Se—, —S— or S—S and $R_{30}$ and $R_{31}$ are independently hydrogen, lower alkyl, or $R_{30}$ and $R_{31}$, together are $(C_3\text{-}C_7)$cycloalkyl, $(C_5\text{-}C_7)$cycloalkenyl, $(C_3\text{-}C_7)$cycloalkyl or $(C_5\text{-}C_7)$cycloalkenyl having one or more hydrogen atoms replaced by halogen atoms, —HC=CHR$_{32}$ and —C=CR$_{33}$ wherein:

$R_{32}$ and $R_{33}$ are independently hydrogen, halogen, tri(lower)alkylsilyl, carboxyl, carbonyl, lower alkoxy, nitrile, sulfinyl lower alkyl, $AXR_{31}$, $A^1\text{—}[Y\text{—}A^{11}]_u\text{—}X\text{—}R_{31}$ or a species represented by the formula:

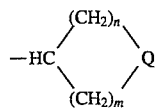

wherein n and m are independently 0 to 6 and Q is —Se—, —SiH$_3$—, —S—, —O— or —NR$_{34}$— wherein $R_{34}$ is hydrogen, lower alkyl or $(C_1\text{-}C_7)$alkanoyl;

or a species represented by the formula:

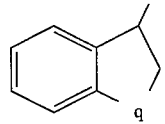

wherein q is —CH$_2$—, —S—, —O— or —NR$_{35}$— wherein $R_{35}$ is hydrogen or lower alkyl;

wherein $R_{17(\beta)}$ is preferably selected from the group consisting of hydrogen, hydroxyl, halogen, alkoxy, $(C_1\text{-}C_7)$alkanoyloxy, $(C_3\text{-}C_7)$alkenoyloxy, $(C_3\text{-}C_7)$alkynoyloxy, cycloalkenyloxy, 1-alkyloxyalkyloxy, 1-alkyloxy cycloalkyloxy, alkylsilyloxy and a divalent common species formed jointly by $R_{17(\alpha)}$ and $R_{17(\beta)}$, said divalent common species being selected from the group consisting of =O, =S, =NR$_{36}$ or =NOR$_{36}$ wherein $R_{36}$ is hydrogen or lower alkyl.

An alternative antiestrogen may be represented by the general formula II:

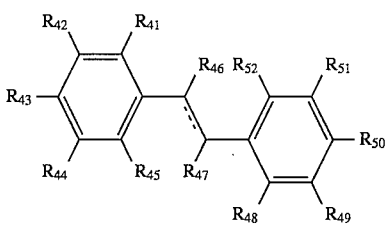

where the dotted lines represent an optional double bond of Z or E configuration;

wherein $R_{41}$, $R_{45}$, $R_{48}$, and $R_{52}$ are independently selected from the group consisting of hydrogen, hydroxyl, halogen, lower alkyl, lower alkoxy, alkylsulfonyl, lower alkoxy, arylsulfonyl lower alkoxy, lower alkylsilyl, amino, nitro, nitrile and nitroso.

wherein $R_{42}$, $R_{44}$, $R_{49}$ and $R_{51}$ are independently selected from the group consisting of hydrogen, hydroxyl, halogen, lower alkyl, lower alkoxy, alkylsulfonyl lower alkoxy, arylsulfonyl lower alkoxy, lower alkylsilyl, amino, nitrile, nitro, nitroso, azido, lower alkylamino, dilower alkylamino, $AXR_{21}$, $Y_{47}$—$A^1$[Y—$A^1$]$_u$—X—$R_{21}$, $A^1$—[Y—$A^{11}$]$_u$ —X—$R_{21}$ wherein:

A, $A^1$, $A^{11}$, X, Y and u are defined as previously in formula I, and $Y_{47}$ is absent or is selected from the group consisting of carbonyl and carboxyl;

wherein $R_{43}$ and $R_{50}$ are independently selected from the group consisting of hydrogen, hydroxyl, halogen, lower alkyl, methoxy, ethoxy, propoxy, hydroxyethoxy, lower alkoxy, lower alkoxy carbonyloxy, carboxyl, acetoxy propionyloxy, butyryloxy, oenanthoyloxy, cypionoyloxy, trans-4-n-butyl-cyclohexanecarbonoyloxy, ($C_1$–$C_{20}$) alkanoyloxy, ($C_3$–$C_{20}$) alkenoyloxy, ($C_3$–$C_{20}$) alkynoyloxy, ($C_7$–$C_{11}$) aroyloxy and alkylsilyloxy;

wherein $R_{46}$ and $R_{47}$ are independently selected from the group consisting of hydrogen, amino, lower alkylamino, dilower alkyl, amino, nitro, nitrile, nitroso, halogen, lower alkyl, lower alkenyl, lower alkynyl, halogeno lower alkyl, halogeno lower alkenyl, halogeno lower alkynyl, alkyl sulfonyl, aryl sulfonyl, a substituted 5- to 7-member heterocyclic ring having at least one heteroatom (selected from oxygen, sulfur, silicon, selenium, nitrogen), —(CH$_2$)$_s$V (wherein V is nitrile, hydroxy, azido, nitroso, alkoxy, nitro, thionitrile, halogen, alkyl sulfonyl or aryl sulfonyl and s is an integer from 1 to 6), a moiety of the formula:

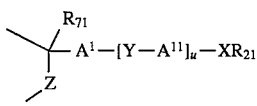 c wherein: F is absent or selected from the group consisting of alkyl, carbonyl or carboxyl, wherein the phenyl ring may be halogenated, wherein $R_{61}$ is selected from the group consisting of hydrogen, hydroxyl, halogen, lower alkyl, lower alkenyl, lower alkynyl, nitrile, nitro, nitroso or $X_{46}$(CH$_2$)$_n$$Y_{46}$ ($X_{46}$ being selected from the group consisting of —O—, —S—, —Se—, —SO—, —SO$_2$— and —CO—, and $Y_{46}$ being selected from the group consisting of hydroxyl, amino, monoalkyl amino, dialkyl amino, dimethyl N-oxide, N-aziridyl, guanidino, N-pyrrolidino, N-piperidino, N-methylpiperazino, N-morpholino and alkoxy, and n being an integer from 1 to 6), $AXR_{21}$, $Y_{47}$—$A^1$—[Y—$A^{11}$]$_u$—X—$R_{21}$ $A^1$—[Y—$A^{11}$]$_u$—X—$R_{21}$ wherein A, $A^1$, $A^{11}$, X, Y, $Y_{47}$ are defined previously for $R_{42}$, $R_{44}$, $R_{49}$ and $R_{51}$;

a species which in combination with another substituent from formula II, forms a moiety selected from the group consisting of —CH$_2$—, —CHX—, —CX$_2$— (X being halogen, carboxyl or alkoxycarbonyl), —O—, —S—, —Se—, >N—CN, >NR$_{29}$ and >NCO$_3$R$_{29}$ (R$_{29}$ being hydrogen or lower alkyl), lower alkylene, —(CH$_2$)$_r$O(CH$_3$)$_s$—, —(CH$_2$)$_r$S(CH$_2$)$_s$—, —(CH$_2$)$_r$ Se(CH$_2$)$_s$—, —(CH$_2$)$_r$SO(CH$_2$)$_s$—, —(CH$_2$)$_r$SO$_2$(CH$_2$)$_s$—, —(CH$_2$)$_r$CO(CH$_2$)$_s$—, —(CH$_2$)$_r$NR$_{22}$(CH$_2$)$_s$—, —(CH$_3$)$_r$SiR$_{22}$R$_{22}$(CH$_2$)$_s$— and —(CH$_2$)$_r$CR$_{22}$OR$_{22}$(CH$_2$)$_s$— (wherein $R_{22}$ being hydrogen or lower alkyl, r and s being independent integers from 0 to 3); a moiety of the formula;

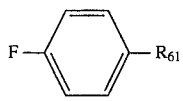 d wherein: Z is absent or is selected from the group consisting of lower alkylene, halogeno lower alkylene, —(CH$_2$)$_n$O—, —(CH$_2$)$_n$S—, —(CH$_2$)$_n$Se—, —(CH$_2$)$_n$SO—, —(CH$_2$)$_n$SO$_2$—, —(CH$_2$)$_n$CO—, —(CH$_2$)$_n$NR$_{22}$—, —(CH$_2$)$_n$SiR$_{22}$R$_{22}$— and —(CH$_2$)$_n$CR$_{22}$OR$_{22}$—, n being an integer from 3, and $R_{71}$ being selected from a group consisting of hydrogen, hydroxyl, halogen, lower alkyl, lower alkoxy and lower alkylsil;

the formula:

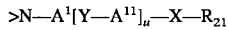

wherein: N is nitrogen atom and $A^1$, Y, $A^{11}$, u, X and $R_{21}$ are defined as previously.

The inhibitors of sex steroid biosynthesis found useful in the present invention include those compounds which inhibit biosynthesis of sex steroids from precursor steroids of adrenal and/or ovarian origin(s) preferably of both ovarian and adrenal origin. Their action can also be exerted in the peripheral tissues, especially in the breast and the endometrium.

Typical inhibitors of sex steroid biosynthesis include but are not limited to 3-(4-aminophenyl)-3-ethyl-2,6-piperidinedione which is commonly called aminoglutethimide, which is an inhibitor of sex steroid biosynthesis of adrenal but also of ovarian and testicular origin and which is available from Ciba Pharmaceutical Co., Summit N.J. under the trade name Cytadren, or ketoconazole, an effective testicular but also adrenal sex steroid biosynthesis, an inhibitor which is available from Janssen Pharmaceuticals, Piscataway, N.J., under the trade name Nizoral.

When an inhibitor of adrenal sex steroid biosynthesis, e.g., aminoglutethimide is administered, cortisol biosynthesis is blocked. Accordingly, a glucocorticoid, e.g. hydrocortisone, is administered in physiological amounts sufficient to maintain normal glucocorticoid activity. Synthetic glucocorticoids can also be used.

The inhibitor of sex steroid formation could also be one or a combination of the above-mentioned steroid and non steroid compound bearing one or more of the alkyl substituents described above.

The inhibitor of sex steroid formation could also be an inhibitor of aromatase activity (4-OH-androstenedione and FCE 34304, as examples) or of 3β-hydroxysteroid, Δ$^5$-Δ$^4$-isomerase activity such as Trilostane, Eposlane or 4-MA, as examples. Of particular interest, 16-methylene estrone and 16-methylene estradiol act as specific inhibitors of 17β-estradiol dehydrogenase (Thomas et al., J. Biol. Chem. 258: 11500–11504, 1983.

Referring to synthesis scheme I below, a preferred antiestrogen which may also act as an inhibitor of sex hormone formation (e.g. inhibitor of estrogen formation) may be prepared as follows:

N-butyl, N-methyl-11-(16α-chloro-3',17'β-dihydroxy-estra-1',3',5'(10')-trien- 7'α-yl) undecanamide ("EM 139", Scheme 1)

N-butyl, N-methyl-11-(3',17'-diacetoxy-estra-1',3',5'(10'), 16'-tetraen- 7'α-yl) undecanamide (3)

To 11-(3-benzoyloxy-17-oxo-estra-1,3,5(10)-trien-7α-yl) undecanoic acid (1) (3.94 g, 7.22 mmol), prepared as described (Bucourt et al., J. Biol. Chem. 253: 8221–8228, 1978), dissolved in anhydrous $CH_3Cl_2$ (100 ml) and cooled at $-10°$ C. was added tributylamine (2.18 ml, 9.15 mmol) and isobutylchloroformate (1.30 ml, 10.0 mmol). The solution was stirred during 35 min. and N-methylbutylamine (13 ml, 109.7 mmol) was added. The mixture was warmed to room temperature and stirred during 1 h. Afterward, $CH_2C_3$ was added and the organic phase was washed with 1N HCl, water, saturated sodium bicarbonate solution and finally with water, dried with anhydrous $MgSO_4$ and the solvent was removed under reduced pressure. The residue was purified by chromatography on silica gel. Elution with mixture of EtOAc/hexane (1.5:8.5 v/v) yielded N-butyl, N-methyl-11-(3'-benzoyloxy- 17'-oxo-estra-1',3',5'(10')-trien-7'α-yl) undecanamide (4.25 g, 96%) as colorless oil; TR ν (neat) 1750, 1725 and 1640 $cm^{-1}$. The above described benzoyloxy amide (341 mg, 0.54 mmol) was dissolved in methanol (10 ml) and cooled at $0°$ C. Following this 2N NaOH (5 ml) was added and the mixture was stirred during 60 min. at $0°$ C. The solution was neutralized with 1N HCl and extracted with $CH_2Cl_2$. The organic phase was dried with anhydrous $MgSO_4$ and the solvent was removed under reduced pressure. The residue was purified by chromatography on silica gel. Elution with mixture of EtOAc/hexane (3:7 v/v) yielded N-butyl, N-methyl-11-(3'-hydroxy-17'-oxo-estra- 1',3',4'(10')-trien-7'α-yl) undecanamide (2) (294 mg, 97%) as colorless oil; $^1$H-NMR o ($CDCl_3$) 0.91 (s, 3H,18'-$CH_3$), 2.76 app (d, 1HJ=16, 3 Hz, part of ABX system, 6'-H) 2.96 and 2.98 (2 s, 3 H N-$CH_3$), 3.27 and 3.38 (2 $t_{app}$, 2H, J=7.5 Hz, N—$CH_2$—), 6.63 (broad s, 1H, 4'-H), 6.70 (broad d, 1H, J=8.5 Hz, 2'-H), 7.12 (d, 1H, J=8.4 Hz, 1'-H); IR ν (neat) 3270, 1730, 1615 $cm^{-1}$; MS m/e 523 ($M^+$, 100%), 508 ($M^+$—$CH_3$, 32%), 142 ($C_2H_4CON(CH_2)C_4H_5^+$, 47%). The ketone amide 2 (163 mg, 0.50 mmol) was dissolved in isoprenyl acetate (10 ml). p-Toluenesulfonic acid (44 mg) was then added and the solution was distilled to about two-thirds of the original volume in 7 hrs and was then stirred at reflux for 12 hrs. Afterwards, the solution was cooled with an ice-water bath and extracted with 50 ml of cooled ether. The ether was washed with a cooled saturated sodium bicarbonate and water. The organic phase was dried with anhydrous $MgSO_4$ and the solvent was removed under reduced pressure. The residue was filtered through alumina (15 mm×50 mm alumina Woehlm neutral, activity II) using a mixture of benzene-diethyl ether (3:7 v/v) as eluent. The solvent was removed under reduced pressure and, the residue was purified by flash chromatography on silica gel. Elution with mixture of EtOAc/hexane (1:4 v/v) yielded the N-butyl, N-methyl-11-(3',17'-diacetoxy-estra-1',3',5'(10'), 16'-tetraen-7'α-yl) undecamide (3) (244 mg, 80%) as colorless oil; $^1$H-NMR δ($CDCl_3$) 0.92 (s, 3H, 18'-$CH_3$), 0.92 and 0.95 (2 t, 3 H, J=7.0 Hz, N($CH_2$)$_3$$\underline{CH_3}$), 2.18 (s, 3H, 17'-OCO$\underline{CH_3}$), 2.28 (s, 3H, 3'-OCO$CH_3$), 2.76 app (d, 1 H, J=16.1 Hz, part of ABX system, 6'-H), 2.90 and 2.96 (2 s, 3 H, N—$CH_3$), 3.26 and 3.35 (2 $t_{app}$, 2 H, J=7.6 Hz, N—$CH_2$—), 5.52 (m, 1 H, 16'-H), 6.80 (broad s, 1 H, 4'-H), 6.85 (dd, 1 H, $J_1$=9.1 Hz and $J_2$=3.0 Hz, 2'-H), 7.27 (d, 1 H, J=9.1 Hz, 1'-H); IR ν (neat) 1750, 1635, 1200 $cm^{-1}$; MS m/e 607 ($M^+$, 2%), 565 ($M^+$—$COCH_3$, 100%), 550 ($M^+$—$COCH_2$—$CH_3$, 13%), 523 ($M^+$—2$COCH_2$, 45%), 142 ($C_2H_4CON(CH_3)C_4H_5^+$,55%), 129 ($C_4H_9(CH_3)NCOCH_3^+$, 38%), 114 ($C_4H_9(CH_3)NCO^+$,60%), 86 ($C_4H_9(CH_3)N^+$, 25%); EXACT MASS calcd for $C_{38}H_{37}O_5N$ 607, 4239, found 607.4234.

The N-butyl, N-methyl-11-(16'α-chloro-3'acetoxy-17'-oxo-estra-1',3',4'(10')-triene-7'α-yl) undecanamide (4)

To diacetate amide 3, dissolved in 5 ml of acetone, was added a solution of sodium acetate (2.6 equivalents) in acetic acid and eater (1:11.3 v/v) and then, was treated with tertbutyl hypochlorite (1 eq.) prepared from t-butanol (4 ml) and Javel water (Javex 6.1%, 50 ml). The clear solution was warmed to $55°$ C. and stirred for 1 h. Afterwards, the solvent was evaporated to dryness. The residue was dissolved in ether (100 ml) and water was added (20 ml). The organic phase was washed with water, dried with anhydrous $MgSO_4$ and evaporated to dryness. The residue was purified by chromatography on silica gel carried out with mixture of EtOAc/hexane, (3:7 v/v) to give the N-butyl, N-methyl-11-(16'α-chloro- 3'acetoxy-17'-oxo-estra-1',3',4'(10')-trien-7'α-yl) undecanamide (4) (115 mg, 89%) as colorless oil; $^1$H-NMR δ($CDCl_3$) 0.92 and 0.95 (2 t, 3 H, J=7.0 Hz, N($CH_2$)$_3$$\underline{CH_2}$). 0.96 (s, 3 H, 18'-$CH_3$), 2.28 (s, 3 H, 3'-OCO$CH_2$), 2.80 app (d, 1 H, J=16,6 Hz, part of ABX system, 6'-H) 2.90 and 2.96 (2 s, 3 H, N—$CH_2$), 3.24 and 3.35 (2 $t_{app}$,2 H, J=7.4 Hz, —N—$CH_2$—), 4.46 (d, 1 H, J=6.6 Hz, 16'β-H), 6.82 (broad, s, 1 H, 4'-H), 6.86 (dd, 1 H, $J_1$=9.1 Hz and $J_2$=2.6 Hz, 2'-H), 7.29 (d, 1 H, J=9.1 Hz, 1'-H); IR (neat) 1750, 1640, 1205 $cm^{-1}$; MS m/e 601, 599 ($M^+$, 24%, 68%), 142 ($C_2H_4CON(CH_3)C_4H_9^+$, 100%), 114 ($C_4H_9(CH_3)NCO^+$, 93%).

N-butyl, N-methyl-11-(16α-chloro-3',17'β-dihydroxy-estra-1',3',5'(10')-trien- 7'α-yl) undecanamide ("EM 139")

A stirred solution of haloketone amide 4 in anhydrous tetrahydrofuran (THF) (10 ml) under argon was chilled to $-70°$ C. with 2-propanol/dry ice bath to $-70°$ C. with 2-propanol/dry ice bath. A solution of 1.0M of lithium aluminium hybride (2 eq.) was then added dropwise. After 30 min. the reaction was allowed to return slowly at $0°$ C. for 5 min, then was quenched by the dropwise addition of a mixture of THF-EtOAc (5 ml) (1:1 v/v) and acidified at pH ~4 with (10%) HCl. The mixture was stirring for 5 min. at room temperature and then extracted with EtOAc. The organic phase was washed with water, dried on anhydrous $Na_2SO_4$ and evaporated under reduced pressure. The residue included two important antiestrogens which were separated by chromatography on silica gel and eluted with a mixture of EtOAc/hexane (4:6 v/v):

N-butyl, N-methyl-11-(16'α-chloro-3',17'α-dihydroxy-estra-1',3',5'(10')-trien- 7'α-yl) undecanamide ("EM 17") (15 mg, 29%) as colorless oil; analytical sample was obtained by HPLC purification; $^1$H-NMR δ($CDCl_3$, 400 MHz) 0.79 (s, 3 H, 18'-$CH_2$), 0.93 and 0.96 (2 t, 3 H, J=7.3 Hz, N($CH_2$)$_2$$\underline{CH_2}$), 2.80 (2 H, $J_{6,6}$=17.1 Hz and $J_{6,7}$=4.5 Hz, Δδ=24,34 (Hz, system ABX, 6'-H), 2.94 and 2.99 (2 s, 3 H, N—$CH_3$), 3.26 (dd, $J_1$=7.6 Hz and $J_2$=7.4 Hz) and 3.32–3.43 (m)-[2H, —N—$CH_2$—], 3.71 (d, 1 H, J=4.5 Hz, 17'β-H), 4.63 (ddd, 1 H, $J_{15,16}$=10.2 Hz, $J_{16,17}$=4.5 Hz and $J_{15,16}$ 3.9 Hz, 16'β-H), 6.50 (d, 1 H, J=24 Hz, 3'-OH), 6.60 (d, 1 h, J=2.5 Hz, 4'-H), 6.66 (dd, 1 H, $J_1$=8.4 Hz and $J_2$=2.5 Hz, 2'-H), 7.14 (d, 1H, J=8.5 Hz, 1'-H); IR ν (neat) 3300, 1615, 1495 $cm^{-1}$; MS m/e 561, 559 ($M^+$, 40%, 100%), 523 ($M^+$-HCl, 20%), 142 ($C_2H_4CON(CH_3)C_4H_9^+$, 44%), 114 ($C_4H_9(CH_3)CNO^+$, 37%); Exact mass calculated for $C_{34}H_{54}O_3N^{35}Cl$ 559.3821; and -N-butyl, N-methyl-11-(16'α-chloro-3',17'β-dihydroxy-estra-1'3',5'(10')-trien- 7'α-yl) undecamide ("EM 139") (25 mg, 55%) as a colorless oil; analytical sample was obtained by HPLC purification; 1H-NMR δ(CDCl$_3$, 400 MHz), 0.81 (s, 3 H, 18'-CH$_3$), 0.93 and 0.96 (2 t, 3 H, J=7.3 Hz, (CH$_2$)$_2$CH$_2$), 2.78 (2 H, J$_{6,6}$=16.2 Hz and J$_{6,7}$=4.5 Hz, Δ$^5$=24.34 Hz, system ABX, 6'-H), 2.94 and 2.99 (2 s, 3 H, N—CH$_3$), 3.27 (dd, J$_1$=7.6 Hz and J$_2$=7.5 Hz) and 3.31–3.45 (M) [2H, —N—CH$_2$—], 3.86 (dd, 1 H, J$_{17,17'\text{-}OH}$=3.4 Hz and J$_{17,16}$=5.9 Hz, 17'α-H), 4.11 (ddd, 1 H, J$_{16,15}$=10.8 Hz, J$_{16,17}$=5.9 Hz and J$_{15,15}$=2.5 Hz, 16'β-H), 6.56 (d, 1 H, J=19.7 Hz, 3'-OH), 6.61 (d, 1 H, J=2.5 Hz, 4'-H), 6.66 (dd, 1 H, J$_1$=8.4 Hz and H$_2$=2.6 Hz, 2'-H), 7.13 (d, 1 H, J=8.4 Hz, 1'-H); IR ν (neat) 3320, 1615, 1490 cm$^{-1}$; MS m/e 561, 559 (M$^+$, 38%, 100%), 523 (M$^+$-HCl, 16%), 142 (C$_2$H$_4$CON(CH$_3$)C$_4$ H$_9^+$, 80%), 114 (C$_4$H$_9$(CH$_3$)NCO$^+$, 76%): Exact mass calculated for C$_{34}$H$_{54}$O$_3$N$^{35}$Cl 559.3785, found 559.3825.

Scheme 1

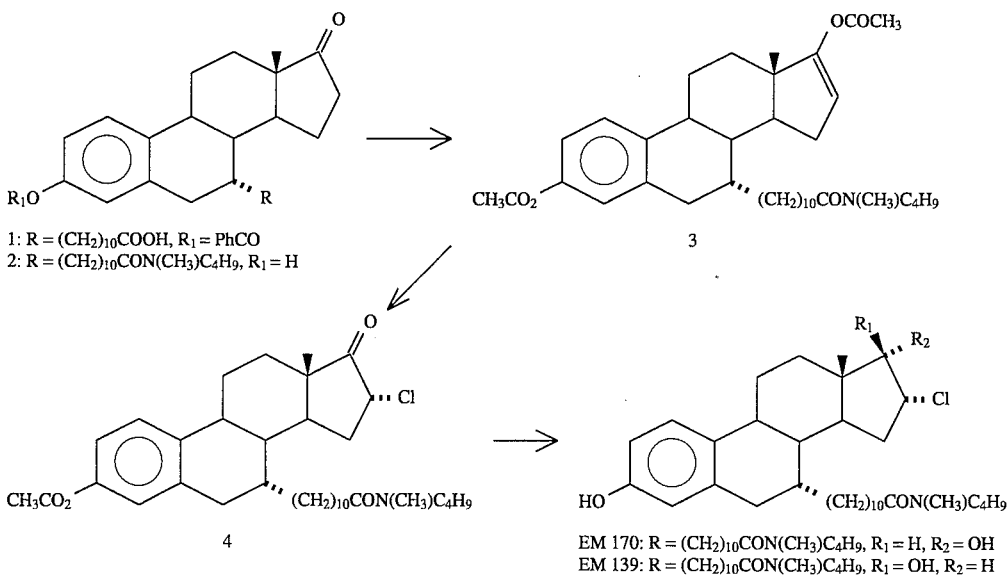

A preferred inhibitor of 17β-estradiol dehydrogenase possesses moreover an antiestrogenic activity and is represented, for example, by the compound of the formula III:

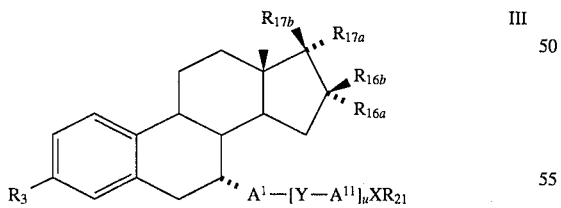

wherein R$_3$ is selected from the group consisting of hydroxyl, halogen, lower alkoxy, methoxy, ethoxy, propoxy, hydroxyethoxy, (C$_2$–C$_{20}$)alkanoyloxy, acetoxy, propionyloxy, butyryloxy, oenanthoyloxy, cypionoyloxy, trans-4-n-butyl-cyclohexanecarbonoyloxy, lower alkoxy carbonyloxy, carboxy, (C$_3$–C$_{20}$)alkenoyloxy, (C$_3$–C$_{20}$)alkynoyloxy, (C$_7$–C$_{10}$)aroyloxy;

wherein R$_{17(\alpha)}$ is selected from the group consisting of hydrogen and hydroxyl;

wherein R$_{15(\alpha)}$ is a halogen, preferably chlorine, fluorine, or bromine; R$_{16(\beta)}$ is preferably hydrogen, or R$_{16(\alpha)}$ and R$_{16(\beta)}$ together form =CG2;

wherein G$_2$ is selected from the group consisting of hydrogen, halogen, lower alkyl, lower alkenyl, lower alkynyl, nitrile, alkoxycarbonyl, alkylcarbonyl and carboxyl;

wherein R$_{17(\beta)}$ is selected from the group consisting of hydrogen, hydroxyl, (C$_1$–C$_7$)alkanoyloxy, (C$_3$–C$_7$)alkenoyloxy, (C$_3$–C$_7$)alkynoyloxy, cycloalkenyloxy, 1-alkyloxy-alkyloxy, 1-alkyloxy cycloalkyloxy, alkylsilyloxy and a divalent common species formed jointly by R$_{17(\alpha)}$ and R$_{17(\beta)}$, said divalent common species being selected from the group consisting of =O, =S, NR$_{36}$ or NOR$_{36}$, wherein R$_{36}$ is hydrogen or lower alkyl;

wherein A$^1$, A$^{11}$, Y, X, R$_{31}$ and u are defined previously in the formula I:

And/or by 16,17-secosteroid derivative of the molecular formula:

IV wherein the dotted lines represent optional double bonds, wherein the A-ring is optionally aromatic;

wherein R$_1$, R$_2$ and R$_4$ are independently selected from the group consisting of hydrogen,m hydroxy, halogen, lower alkyl, lower alkoxy, lower alkylsilyl, amino and nitro;

wherein R$_3$ is selected from the group consisting of hydroxyl, halogen, lower alkoxy, (C$_2$–C$_{20}$)alkanoyloxy, (C$_3$–C$_{20}$)alkenoyloxy, (C$_3$–C$_{20}$)alkynoyloxy, (C$_7$–C$_{10}$)aroyloxy, lower alkoxycarbonyloxy or a divalent common species formed jointly by $R_{3(\alpha)}$ and $R_{3(\beta)}$ said divalent common species being selected from the group consisting of =O, =S, =NR$_{36}$ or =NOR$_{36}$ wherein $R_{36}$ is hydrogen or lower alkyl;

wherein $R_5$ and $R_{10}$ are absent or selected from the group consisting of hydrogen or lower alkyl;

wherein $R_6$ is selected from the group consisting of hydrogen, halogen, lower alkyl, amino or nitrile;

wherein $R_{11}$ is selected from the group consisting of hydrogen, lower alkyl, lower alkynyl, ($C_5$–$C_{10}$)aryl, a substituted 5- to 7-member heterocyclic ring having at least an heteroatom (selected from oxygen, sulfur, silicon, selenium and nitrogen), $(CH_2)_sW$ (wherein W is nitrile, hydroxyl, azido, nitroso, nitro, thionitrile, halogen, alkylsulfonyl or arylsulfonyl, and is an integer from 1 to 6), $OR_{26}$ (wherein $R_{26}$ is hydrogen, lower alkyl or ($C_6$–$C_{10}$)aryl), $DR_{37}$ (wherein D is —Se—, —NR$_{26}$—, —S— or —O—, and $R_{27}$ is hydrogen or lower alkyl), =O, =S, =Se, =NR$_{28}$ and =NOR$_{28}$ (wherein $R_{28}$ is hydrogen or lower alkyl);

wherein $R_{13}$ and $R_{13(\beta)}$ are hydrogen or lower alkyl;

wherein $R_{13(\alpha)}$ is selected from the group consisting of 1-oxo-2-propynyl, 1-hydroxy-2-propynyl, carboxyl, alkoxycarbonyl and alkylcarbonyl;

wherein $R_{14(\alpha)}$ and $R_{14(\beta)}$ are selected from the group consisting of hydrogen, hydroxyl, lower alkyl, lower alkenyl, lower alkynyl and halogeno analogs of the foregoing;

wherein $A^1$, $A^{11}$, Y, n, X, $R^{31}$ are defined as previously in the formula 1.

A preferred inhibitor of prolactin secretion is bromocryptine, e.g. Parlodel (available from Sandoz, Bale, Switzerland). A preferred inhibitor of growth hormone secretion is a somatostatin analogue, e.g. Sandostatin (available from Sandoz, Bale, Switzerland). A preferred inhibitor of ACTH secretion is hydrocortisone acetate, e.g. Solucortef (available from Upjohn).

In this invention, the LHRH agonist or antagonist, antiestrogen, androgen, and, where applicable, the progestin, the inhibitor of steroid biosynthesis (hydrocortisone) and the inhibitor of prolactin and/or growth hormone and/or ACTH secretion are administered as pharmaceutical compositions via topical, parenteral or oral means. The LHRH agonist or antagonist is administered parenterally, i.e., intramuscularly, subcutaneously or intravenously by injection or infusion by nasal drops or by suppository, where applicable intra-vaginally. The LHRH agonist or antagonist may also be microencapsulated in or attached to a biocompatible, biodegradable polymer, e.g., poly(d,1-lactide-co-glycolide) and subcutaneously or intramuscularly injected by a technique called subcutaneous or intramuscular depot to provide continuous, slow release of the LHRH agonist or antagonist over a period of 30 days or longer. The most preferred route of administration of the LHRH agonist or antagonist is subcutaneous depot injection. Preferably the antiestrogen will be administered orally, Preferably, the inhibitors of sex steroid biosynthesis such as aminoglutethimide and ketoconazole, the androgen and progestin, as well as the inhibitor of prolactin, growth hormone and ACTH secretion, when used, are administered orally. The antiestrogen, androgen, progestin and inhibitor of sex steroid formation can also be administered in a slow release formulation, e.g. poly(d,1-lactide-coglycolide) or as implants.

The amount of each component administered is determined by the attending clinicians taking into consideration the etiology and severity of the disease, the patient's condition and age, the potency of each component and other factors. In the combination therapy of breast and endometrial cancer, according to this invention, the following dosage ranges are suitable.

The LHRH agonist or antagonist is generally administered at from about 10 to 5000 µg per day with contemplated dosage ranges of about 10 to 1500 µg per day and about 250 (preferably 200 µg to 500 µg per day) for the LHRH agonist and to about 50 to 5000 µg per day for the LHRH antagonist being preferred.

In the most preferred embodiment of this invention, the LHRH agonist or antagonist is administered subcutaneously in a daily dose of 500 µg of the first 30 days and thereafter subcutaneously in a daily dose of 250 µg regardless of the patients' body weight. When the LHRH agonist or antagonist is administered, once every 30-day period is used, with a dose of 750 to 15,000 µg per 30-day period being preferred. Similar daily delivery doses are used for longer-term controlled release formulations.

The androgen and progestin compositions are generally administered in a dosage range of about 0.10 to 40 mg/kg (body weight) per day with 45 mg per day in three equally divided doses being preferred.

The aminoglutethimide compositions (when used) are administered initially in a dosage of 250 mg given at 8-hour intervals and the dosage may be increased in increments of 250 mg daily up to a total daily dose of 2 grams.

The ketoconazole compositions (when used) are administered orally in a dose of 250 mg given at 8-hour intervals and may be increased to a daily dose of 2 grams.

Other inhibitors of sex steroid biosynthesis are preferably administered in dosages ranging from about 0.1 to 40 mg/kg per day with 45 mg per day in three equally divided doses being preferred.

The antiestrogen compositions are administered in a dosage range of about 0.05 to 25 mg/kg body weight per day, with 10 mg, especially 20 mg, in two equally divided doses being preferred.

The inhibitor of prolactin secretion, bromocriptine, being the example, is administered at the dose of 2 mg once or twice daily. The inhibitor of growth hormone secretion, the somatostatin analog, sandostatin, being an example, is administered subcutaneously at the dose of 100 to 1000 µg per day in these equally divided doses.

The glucocorticoid (also inhibitor of ACTH secretion), especially hydrocortisone compositions (when used), are administered orally in a dosage range of about 0.1 to 20 mg/kg body weight per day. Preferably, the hydrocortisone is administered orally at the dose of about 10 mg in the morning and about 5 mg doses in the afternoon and in the evening.

The LHRH agonist or antagonist, antiestrogen, androgen, progestin and inhibitor of sex steroid biosynthesis as well as the inhibitor of prolactin, growth hormone and ACTH secretion each may be administered separately or when the modes of administration are the same, all or at least two of them may be administered in the same composition, but in any case the preferred ratio of LHRH agonist to antiestrogen, to androgen (when used), to progestin (when used), to inhibitor of sex steroid biosynthesis (when used) administered daily will be about 250 µg of LHRH agonist to about 45 mg of androgen, about 45 mg of progestin, about 15 mg, of antiestrogen, to about 45 mg of inhibitor of sex steroid biosynthesis at about 750 mg of inhibitor of adrenal steroid secretion.

In the therapy of breast and endometrial cancer, combining the administration of an LHRH agonist or antagonist, an antiestrogen, an androgen, and a progestin, the dosages preferable are as follows: the LHRH agonist or antagonist is generally administered at from about 10 to 2000 μg per day, with contemplated dosage ranges of 10 to 500 μg per day, 50–250 μg per day and 250 to 500 μg per day being preferred. In the most preferred embodiment of this aspect of this invention, the LHRH agonist or antagonist is administered subcutaneously in a daily dose of 500 μg for the first 30 days and thereafter subcutaneously in a daily dose of 250 μg regardless of the patients' body weight. When the LHRH agonist or antagonist is administered, once every 30-day period, by intramuscular or subcutaneous depot injection, a dose from about 300 to 60000 (occasionally 15000) μg per 30-day period is used, with a dose of 750 to 6000 μg per 30-day period being preferred. The androgen and progestin compositions are generally administered in a dosage range of about 0.10 to 40 mg/kg (body weight) per day with 45 especially 75 mg per day in three equally divided doses being preferred. The antiestrogen and inhibitor of sex steroid formation compositions are administered in a dosage range of about 0.1 to 25 mg/kg body weight per day, with 10 mg in three, preferably with 20 mg in two, equally divided doses being preferred. The aminoglutethimide compositions when used are administered initially in a dosage of 250 mg given at preferably 8-hour intervals and the dosage may be increased in increments of 250 mg daily up to a total daily dose of 2 grams. The ketoconazole compositions when used are administered orally in a dose of 250 mg twice daily and may be increased to 200 mg, four times a day.

The LHRH agonist or antagonist, antiestrogen, androgen, progestin and inhibitor of sex steroid formation, each may be administered separately or when the modes of administration are the same, all or two or three of them may be administered in the same composition, but in any case the preferred ratio of LHRH agonist to androgen (or progestin) to antiestrogen administered daily will be about 250 μg of LHRH agonist to about 45 mg of androgen and progestin to preferably 20 mg of antiestrogen.

In the therapy of breast and endometrial cancer, according to this invention, it is preferred that the LHRH agonist is [D-Trp$^5$, des-Gly-NH$_2$$^{10}$]LHRH ethylamide be administered subcutaneously in single daily dose of 500 μg for the first thirty (30) days of treatment and thereafter in a single daily dose of 25 μg; the androgen is MPA which is administered orally in three equally divided daily doses of 15 mg each; and the inhibitor of sex steroid biosynthesis is ketoconazole and/or aminoglutethimide, each of which is administered orally in three equally divided doses of 250 mg every 8 hours; and the hydrocortisone (if used) is administered orally at a dose of about 10 mg in the morning and two equally divided doses of about 5 mg, 8 and 16 hours thereafter; and the antiestrogen is (Z)-2-[4-(1,2-diphenyl-1-butenyl)phenoxyl]-N,N-dimethylethylamine (Tamoxifen) which is administered orally in two equally divided doses of about 10 mg every 12 hours.

In the combination therapy of breast and endometrial cancer according to this invention, the administration of the antiestrogen, androgen, progestin, inhibitor(s) of steroid biosynthesis, glucocorticoid and LHRH agonist or LHRH antagonist can be started in any order of sequence. Preferably, the administration of the androgen and antiestrogen is started before (preferably two to four hours before) the administration of the LHRH agonist or LHRH antagonist is started. Preferably, the administration of the inhibitor(s) of sex steroid biosynthesis is started on the same day as the administration of the LHRH agonist or LHRH antagonist. However, the attending clinician may elect to start administration of the LHRH agonist or antagonist simultaneously with the androgen, progestin and inhibitor of sex steroid function.

When patients whose ovaries have already been surgically removed are treated according to this invention, the administration and dosage of the androgen and the other components of the therapy (except the LHRH agonist or antagonist which is not used) are the same as indicated for the therapy in which the LHRH agonist or antagonist is used.

The LHRH agonists or antagonists useful in the present invention are typically amorphous solids which are freely soluble in water or dilute acids, e.g., HCl, $H_2SO_4$, citric, acetic, mandelic or fumaric. The LHRH agonist or antagonist for subcutaneous injection is supplied in vials containing 5 ml of sterile solution with the LHRH agonist or antagonist at a concentration of about 1.0 mg/ml.

A typical pharmaceutical composition of the LHRH agonist or antagonist includes the LHRH agonist or antagonist or a pharmaceutically acceptable acid salt thereof, benzyl alcohol, a phosphate buffer (pH 6.0–6.5) and sterile water.

The LHRH agonist or antagonist for intramuscular or subcutaneous depot injection may be microencapsulated in a biocompatible, biodegradable polymer, e.g., poly (d,1-lactide-co-glycolide) by a phase separation process or formed into a pellet. The microspheres may then be suspended in a carrier to provide an injectable preparation or the depot may be injected in the form of a pellet. See also European patent application EPA No. 58,481 published Aug. 25, 1982 for solid compositions for subdermal injection or implantation or liquid formulations for intramuscular or subcutaneous injections containing biocompatible, biodegradable polymers such as lactide-glycolide copolymer and an LHRH agonist, e.g. D-Ser-t-BuO$^6$, Azgly$^{10}$-LHRH. These formulations permit controlled release of the peptide.

The inhibitors of sex steroid biosynthesis, e.g., aminoglutethimide and ketoconazole and the glucocorticoid, e.g., hydrocortisone (when used) are typically compounded in customary ways for oral administration, e.g., in tablets, capsules and the like.

The androgen and progestin useful in the present invention are typically formulated with conventional pharmaceutical excipients, e.g., spray dried lactose and magnesium stearate into tablets or capsules for oral administration. The antiestrogens, when used with the invention, are typically compounded in customary ways for oral administration, e.g., in capsules, tablets, as dragees or even in liquid form, e.g., suspensions or syrups. One or more of the active substances, with or without additional types of active agents, can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycols. Of course, taste-improving substances can be added in the case of oral administration forms.

The therapeutically active antiestrogen compound should be present in a concentration of about 0.5–90% by weight of the total mixture, i.e., in amounts that are sufficient for maintaining the above-mentioned dosage range.

As further forms, one can use plug capsules, e.g., of hard gelatin, as well as closed soft-gelatin capsules comprising a softener or plasticizer, e.g. glycerine. The plug capsules contain the active substance preferably in the form of granulate, e.g., in mixture with fillers, such as lactose, saccharose, mannitol, starches, such as potato starch or amylopectin, cellulose derivatives or highly-dispersed silicic acids. In soft-gelatin capsules, the active substance is preferably dissolved or suspended in suitable liquids, such as vegetable oils or liquid polyethylene glycols.

In place of oral administration, the active compounds may be administered parenterally. In such case, one can use a solution of the active substance, e.g., in sesame oil or olive oil. One or more of the active substances (androgen, antiestrogen, progestin and/or inhibitor of sex steroid formation) can be microencapsulated in or attached to a biocompatible, biodegradable polymer, e.g. poly(d,1-lactide-co-glycolide) and subcutaneously or intramuscularly injected by a technique called subcutaneous or intramuscular depot to provide continuous slow release of the compound(s) for a period of 2 weeks or longer.

The invention also provides kits or single packages combining the pharmaceutical compositions useful for the combination treatment of breast and endometrial cancer discussed above. The kits or packages may also contain instructions to use the pharmaceutical compositions in accordance with the present invention. This aspect of the invention is exemplified by the following discussions: for the treatment of breast or endometrial cancer, a four-component kit provides an antiestrogen, an androgen and an inhibitor of sex steroid formation oral pharmaceutical compositions and an LHRH agonist or LHRH antagonist parenteral composition while a three-component kit could be an antiestrogen, an androgen oral pharmaceutical composition or the oral compositions of an antiestrogen and an inhibitor of sex steroid biosynthesis with the LHRH agonist or LHRH antagonist parenteral composition.

Following the above treatment using the described regimen, tumor growth and bone metastases of breast and endometrial cancer are inhibited and in some instances complete remission may occur.

The terms and descriptions used herein are preferred embodiments set forth by way of illustration only, and are not intended as limitations on the many variations which those of skill the art will recognize to be possible in practicing the present invention as defined by the following claims.

What is claimed is:

1. A method of treating breast or endometrial cancer comprising the steps of inhibiting the ovarian hormonal secretions of a warm blooded patient in need of such treatment and administering to said patient therapeutically effective amounts of an antiestrogen and at least one compound selected from the group consisting of an androgenic compound and, an inhibitor of an enzyme that catalyzes a step in the synthesis of sex steroids from sex steroid precursors in peripheral tissues, said inhibitor achieving that result by a non-adrenal mechanism.

2. The method of claim 1, wherein said method includes administering said non-adrenal inhibitor.

3. The method of claim 2, wherein said non-adrenal inhibitor is an inhibitor of aromatase.

4. The method of claim 2, wherein said non-adrenal inhibitor is an inhibitor of either 3β-hydroxysteroid dehydrogenase or 17β-hydroxysteroid dehydrogenase.

5. The method of claim 1, wherein said method includes both the steps of administering said androgenic compound and administering said non-adrenal inhibitor.

6. The method of claim 5, wherein said non-adrenal inhibitor is an inhibitor of aromatase, and said androgenic compound is a progestin.

7. The method of claim 1, wherein said androgenic compound is a progestin.

8. A kit for treatment of breast or endometrial cancer, said kit including a pharmaceutical composition comprising an antiestrogen and further including a pharmaceutical composition comprising an inhibitor of an enzyme that catalyzes a step in the synthesis of sex steroids from sex steroid precursors in peripheral tissues, said inhibitor achieving that result by a non-adrenal mechanism.

9. The kit of claim 8 further comprising an inhibitor of ovarian hormonal secretions.

10. The kit of claim 9 further comprising an androgenic compound.

11. The kit of claim 10, wherein said non-adrenal inhibitor is an inhibitor of aromatase and wherein said androgenic compound is a progestin.

12. The kit of claim 8 further comprising a progestin or androgen.

13. The kit of claim 8, wherein said non-adrenal inhibitor is an inhibitor of aromatase.

14. The kit of claim 8, wherein said non-adrenal inhibitor is an inhibitor of either 3β-hydroxysteroid dehydrogenase or 17β-hydroxysteroid dehydrogenase.

15. A method of treating breast or endometrial cancer in a warm-blooded animal, wherein said method comprises administering to said animal therapeutically effective amounts of an antiestrogen and of an inhibitor of an enzyme that catalyzes a step in the synthesis of sex steroids from sex steroid precursors in peripheral tissues, said inhibitor achieving that result by a non-adrenal mechanism.

16. The method of claim 15, wherein said method includes administering at least one compound selected from the group consisting of an inhibitor of growth hormone secretion and an inhibitor of ACTH secretion.

17. The method of claim 15, wherein said non-adrenal inhibitor of sex steroid formation is selected from the group consisting of an inhibitor of 17β-hydroxysteroid dehydrogenase, an inhibitor of 3β-hydroxysteroid dehydrogenase and an inhibitor of aromatase.

18. The method of claim 15 further comprising inhibiting ovarian hormonal secretions.

19. The method of claim 18 further comprising administering an androgenic compound.

20. The method of claim 19, wherein said non-adrenal inhibitor is an inhibitor of aromatase and wherein said androgenic compound is a progestin.

21. The method of claim 15 further comprising administering a progestin or androgen.

22. The method of claim 15, wherein said non-adrenal inhibitor is an inhibitor of aromatase.

23. The method of claim 15, wherein said non-adrenal inhibitor is an inhibitor of either 3β-hydroxysteroid dehydrogenase or 17β-hydroxysteroid dehydrogenase.

24. A therapeutic pharmaceutical composition for treatment of breast or endometrial cancer, said pharmaceutical composition comprising a therapeutically effective amount of an antiestrogen and of an inhibitor of an enzyme that catalyzes a step in the synthesis of sex steroid from sex steroid precursors in peripheral tissues, said inhibitor achieving that result by a non-adrenal mechanism.

25. The composition of claim 24 wherein said composition includes an inhibitor of ACTH secretion or an inhibitor of growth hormone secretion.

26. The composition of claim 24, wherein the non-adrenal inhibitor of sex steroid formation is selection from the group consisting of an inhibitor of 17β-hydroxysteroid dehydrogenase, an inhibitor of 3β-hydroxysteroid dehydrogenase and an inhibitor of aromatase.

27. The pharmaceutical composition of claim 24, further comprising an inhibitor of ovarian hormonal secretions.

28. The pharmaceutical composition of claim 27 further comprising an androgenic compound.

29. The pharmaceutical composition of claim 28, wherein said non-adrenal inhibitor is an inhibitor of aromatase and wherein said androgenic compound is a progestin.

30. The pharmaceutical composition of claim 24, further comprising a progestin or androgen.

31. The pharmaceutical composition of claim 24, wherein said non-adrenal inhibitor is an inhibitor of aromatase.

32. The pharmaceutical composition of claim 24, wherein said non-adrenal inhibitor is an inhibitor of either 3β-hydroxysteroid dehydrogenase or 17β-hydroxysteroid dehydrogenase.

33. A kit of treatment of breast or endometrial cancer, said kit including a pharmaceutical composition comprising an inhibitor of ovarian hormonal secretions, a pharmaceutical composition comprising an antiestrogen, and a pharmaceutical composition comprising at least one compound selected from the group consisting of an androgenic compound and an inhibitor of an enzyme that catalyzes a step in the synthesis of sex steroids from sex steroid precursors in peripheral tissues, said inhibitor achieving that result by a non-adrenal mechanism.

34. The kit of claim 33, wherein said kit includes a non-adrenal inhibitor.

35. The kit of claim 34, wherein said non-adrenal inhibitor is an inhibitor of aromatase.

36. The kit of claim 34, wherein said non-adrenal inhibitor is an inhibitor of either 3β-hydroxysteroid dehydrogenase or 17β-hydroxysteroid dehydrogenase.

37. The kit of claim 33, wherein said kit includes both said androgenic compound and said non-adrenal inhibitor.

38. The kit of claim 37, wherein said non-adrenal inhibitor is an inhibitor of aromatase, said androgenic compound is a progestin.

39. The kit of claim 33, wherein said androgenic compound is a progestin.

40. A pharmaceutical composition for treatment of breast or endometrial cancer including a pharmaceutically acceptable diluent or carrier and a therapeutically acceptable amount of (A) an inhibitor of ovarian hormonal secretions, (B) an antiestrogen, and (C) at least one pharmaceutical compound selected from the group consisting of an androgenic compound and an inhibitor of an enzyme that catalyzes a step in the synthesis of sex steroids from sex steroid precursors in peripheral tissues, said inhibitor achieving that result by a non-adrenal mechanism.

41. The pharmaceutical composition of claim 40, wherein said composition includes said non-adrenal inhibitor.

42. The pharmaceutical composition of claim 41, wherein said non-adrenal inhibitor is an inhibitor of aromatase.

43. The pharmaceutical composition of claim 41, wherein said non-adrenal inhibitor is an inhibitor of either 3β-hydroxysteroid dehydrogenase or 17β-hydroxysteroid dehydrogenase.

44. The pharmaceutical composition of claim 40, wherein said composition includes both said androgenic compound and said non-adrenal inhibitor.

45. The pharmaceutical of claim 44, wherein said non-adrenal inhibitor is an inhibitor of aromatase and said androgenic compound is a progestin.

46. The pharmaceutical composition of claim 40, wherein said androgenic compound is a progestin.

* * * * *

UNITED STATES PATENT AND TRADEMARK OFFICE
CERTIFICATE OF CORRECTION

PATENT NO. : 5,550,107
DATED : August 27, 1996
INVENTOR(S) : Fernand LABRIE

It is certified that error appears in the above-indentified patent and that said Letters Patent is hereby corrected as shown below:

Column 25, line 51, change "by a non-adrenal mechanism" to --without suppressing adrenal activity--;
    line 53, change "non-adrenal" to --enzyme--;
    line 54, change "non-adrenal" to --enzyme--;
    line 56, change "non-adrenal" to --enzyme--;
    line 61, change "non-adrenal" to --enzyme--;
    line 62, change "non-adrenal" to --enzyme--.

Column 26, line 6, change "by a non-adrenal mechanism" to --without suppressing adrenal activity--;
    line 11, change "non-adrenal" to --enzyme--;
    line 16, change "non-adrenal" to --enzyme--;
    line 18, change "non-adrenal" to --enzyme--;
    line 27, change "by a non-adrenal mechanism" to --without suppressing adrenal activity--;
    lines 32 - 33, change "non-adrenal inhibitor of sex steroid formation" to --enzyme inhibitor--;
    line 41, change "non-adrenal" to --enzyme--;
    line 46, change "non-adrenal" to --enzyme--;
    line 48, change "non-adrenal" to --enzyme--;
    line 57, change "by a non-adrenal mechanism" to --without suppressing adrenal activity--;
    lines 61 - 62, change "non-adrenal inhibitor of sex steroid formation is selection" to --enzyme inhibitor is selected--.

UNITED STATES PATENT AND TRADEMARK OFFICE
CERTIFICATE OF CORRECTION

PATENT NO. : 5,550,107
DATED : August 27, 1996
INVENTOR(S) : Fernand LABRIE

It is certified that error appears in the above-indentified patent and that said Letters Patent is hereby corrected as shown below:

Column 27,     line 4, change "non-adrenal" to --enzyme--;
                 line 9, change "non-adrenal" to --enzyme--;
                 line 11, change "non-adrenal" to --enzyme--;
                 lines 22 - 23, change "by a non-adrenal mechanism" to --without suppressing adrenal activity--;
                 lines 24 - 25, change "a non-adrenal" to --an enzyme--;
                 line 26, change "non-adrenal" to --enzyme--;
                 line 28, change "non-adrenal" to --enzyme--;
                 line 32, change "non-adrenal" to --enzyme--;
                 line 33, change "non-adrenal" to --enzyme--.

UNITED STATES PATENT AND TRADEMARK OFFICE
CERTIFICATE OF CORRECTION

PATENT NO. : 5,550,107
DATED : August 27, 1996
INVENTOR(S) : Fernand Labrie

It is certified that error appears in the above-indentified patent and that said Letters Patent is hereby corrected as shown below:

Column 28, line 15, change "by a non-adrenal mechanism" to --without suppressing adrenal activity--;
  line 17, change "non-adrenal" to --enzyme--;
  line 19, change "non-adrenal" to --enzyme--;
  line 21, change "non-adrenal" to --enzyme--;
  line 26, change "non-adrenal" to --enzyme--;
  lines 27 - 28, change "non-adrenal" to --enzyme--.

Signed and Sealed this

Twenty-ninth Day of April, 1997

Attest:

BRUCE LEHMAN

Attesting Officer

Commissioner of Patents and Trademarks